US009180122B2

(12) United States Patent
Farnaby et al.

(10) Patent No.: US 9,180,122 B2
(45) Date of Patent: Nov. 10, 2015

(54) 5- OR 6-SUBSTITUTED 3-HYDROXY-2 (1 H)-PYRIDINONES AS D-AMINO ACID OXIDASE (DAAO) INHIBITORS IN THERAPY OF DISEASES SUCH AS SCHIZOPHRENIA, COGNITIVE DISORDER AND PAIN

(75) Inventors: William Farnaby, Cambridge (GB); Charlotte Fieldhouse, Cambridge (GB); Catrina Kerr, Dundee (GB); Natasha Kinsella, Kampala (UG); David Livermore, Cambridge (GB); Kevin Merchant, Cambridge (GB); David Miller, Cambridge (GB); Katherine Hazel, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/131,343

(22) PCT Filed: Jul. 5, 2012

(86) PCT No.: PCT/GB2012/000574
§ 371 (c)(1),
(2), (4) Date: May 8, 2014

(87) PCT Pub. No.: WO2013/004996
PCT Pub. Date: Jan. 10, 2013

(65) Prior Publication Data
US 2014/0243353 A1  Aug. 28, 2014

(30) Foreign Application Priority Data
Jul. 7, 2011 (GB) .................................. 1111704.1

(51) Int. Cl.
| | |
|---|---|
| A61K 31/4412 | (2006.01) |
| A61K 31/444 | (2006.01) |
| A61K 31/497 | (2006.01) |
| A61K 45/06 | (2006.01) |
| C07D 213/69 | (2006.01) |
| C07D 213/70 | (2006.01) |
| C07D 213/71 | (2006.01) |
| C07D 401/12 | (2006.01) |
| C07D 413/12 | (2006.01) |

(52) U.S. Cl.
CPC ........... *A61K 31/4412* (2013.01); *A61K 31/444* (2013.01); *A61K 31/497* (2013.01); *A61K 45/06* (2013.01); *C07D 213/69* (2013.01); *C07D 213/70* (2013.01); *C07D 213/71* (2013.01); *C07D 401/12* (2013.01); *C07D 413/12* (2013.01)

(58) Field of Classification Search
CPC ............ A61K 31/4412; A61K 31/444; A61K 31/497; A61K 45/06; C07D 213/69; C07D 213/70; C07D 213/71; C07D 401/12; C07D 413/12
See application file for complete search history.

(56) References Cited

U.S. PATENT DOCUMENTS

| | | |
|---|---|---|
| 4,193,916 A | 3/1980 | Back et al. |
| 4,734,496 A | 3/1988 | Breuer et al. |
| 5,244,890 A | 9/1993 | Yamanaka et al. |
| 5,401,734 A | 3/1995 | Yamanaka et al. |
| 5,532,354 A | 7/1996 | Yamanaka et al. |
| 5,962,480 A | 10/1999 | Moriguchi et al. |
| 2010/0022526 A1 | 1/2010 | Lamberth et al. |
| 2013/0052281 A1 | 2/2013 | Farnaby et al. |
| 2014/0248378 A1 | 9/2014 | Cockcroft et al. |
| 2015/0030704 A1 | 1/2015 | Farnaby et al. |

FOREIGN PATENT DOCUMENTS

| | | |
|---|---|---|
| BE | 859 477 | 4/1978 |
| DE | 2745024 | 10/1977 |
| EP | 0180 298 | 5/1986 |
| EP | 0 593 110 | 4/1994 |
| EP | 2 314 586 A1 | 4/2011 |
| GB | 2 025 416 | 1/1980 |

(Continued)

OTHER PUBLICATIONS

Nakamura, et al., Studies on Prototropic Tautomerism in Nitrogen Heterocyclic Compounds. II. A Ring-Chain Tautomerism in 3-Hydroxy-6-(2-oxocycloalkyl)-methyl-2(IH)-pyridone and 3-Hydroxy-6-(3-oxoalkyl)-2(IH)-pyridone Derivatives, Chem. Pharm. Bull., vol. 17, No. 3, pp. 425-433 (1969).*
Nakamura, et al., Studies on Prototropic Tautomerism in Nitrogen Heterocyclic Compounds. I, Chem. Pharm. Soc., vol. 16, No. 8, pp. 1466-1471 (1968).*
Dyumaev, et al., Aminomethylation of 2,3-dihydroxy- and 3-hydroxy-2-methoxypyridine, XP002684179, Chemical Abstracts Service, Columbus, OH (1972).*
International Search Report, PCT/GB2012/000574, Oct. 11, 2012.
Adage T., et al., "In vitro and in vivo pharmacological profile of AS057278, a selective D-amino acid oxidase inhibitor with potential anti-psychotic properties," European Neuropsychopharmacology 2008, 18, pp. 200-214.
Sparey T., et al., "The discovery of fused pyrrole carboxylic acids as novel, potent D-amino acid oxidase (DAO) inhibitors," Bioorganic & Medicinal Chemistry Letters, 2008, 18, pp. 3386-3391.

(Continued)

*Primary Examiner* — Erich A Leeser
(74) *Attorney, Agent, or Firm* — Finnegan, Henderson, Farabow, Garrett & Dunner, L.L.P.

(57) ABSTRACT

The present invention provides compounds of formula (I) and pharmaceutically acceptable salts thereof, wherein $R^1$ is hydrogen or fluorine, one of A and B is R2, the other is a group —X—Y—R3. R3 represents a carbocyclic or heterocyclic ring. Further variables are as defined in the specification. Also claimed are—processes for their preparation, pharmaceutical compositions containing them and their use in therapy of diseases such as schizophrenia, cognitive disorders and pain by modulating the D-amino acid oxidase enzyme (DAAO).

(I)

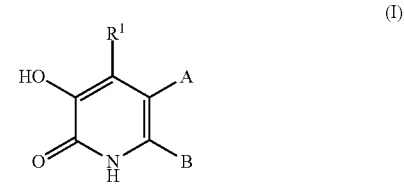

28 Claims, No Drawings

(56) References Cited

FOREIGN PATENT DOCUMENTS

| | | |
|---|---|---|
| JP | 62-84082 | 4/1987 |
| JP | 2002-028187 | 1/1990 |
| JP | 2009-025234 | 1/1997 |
| JP | 2007-517056 | 6/2007 |
| WO | WO 02/53543 | 7/2002 |
| WO | WO 03/062233 | 7/2003 |
| WO | WO 2004/094408 | 11/2004 |
| WO | WO 2005/061458 | 7/2005 |
| WO | WO 2005/066135 | 7/2005 |
| WO | WO 2006/135828 | 7/2005 |
| WO | WO2008/089453 A2 | 7/2008 |
| WO | WO 2008/115381 | 9/2008 |
| WO | WO 2008/116301 | 10/2008 |
| WO | WO 2008/156607 | 12/2008 |
| WO | WO 2010/017418 | 2/2010 |
| WO | WO 2011/046920 | 4/2011 |
| WO | WO 2011/109254 | 9/2011 |
| WO | WO2011/109261 A1 | 9/2011 |
| WO | WO 2011/109267 | 9/2011 |
| WO | WO 2013/004995 | 1/2013 |
| WO | WO 2013/027000 | 2/2013 |
| WO | WO 2013/073577 | 5/2013 |
| WO | WO 2014/096757 | 6/2014 |

OTHER PUBLICATIONS

Ferraris D., et al., "Synthesis and Biological Evaluation of D-Amino Acid Oxidase Inhibitors," J. Med. Chem., 2008, 51, pp. 3357-3359.
Nakamura A. et al., "Studies on Prototropic Tautomerism in Nitrogen Heterocyclic Compounds. II. A ring-Chain Tautomerism in 3-Hydroxy-6-(2-oxocycloalky)-methyl-2(1H)-pyridone and 3-Hydroxy-6-(3-oxoalkyl)-2(1H)-pyridone Derivatives," Chem. Pharm. Bull., vol. 17, No. 3, 1969, pp. 425-433.
Nakamura A. et al., "Studies of Prototropic Tautomerism in Nitrogen Heterocyclic Compounds. I. The Mannich Reaction of 2(1$H$)-Pyridone and 3-Hydroxy-2(1$H$)-pyridone," Chem. Pharm. Bull. vol. 16, No. 8, 1969, pp. 1466-1471.
Dyumaev, K., et al., "Aminomethylation of 2,3-dihdroxy- and 3-hydroxy-2-methoxypyridine," XP002684179, CAS Database accession No. 1972-564402.
Duplantier A., et al., "Discovery SAR, and Pharmacokinetics of a Novel-3-Hydroxyquinolin-2(1$H$)-one Series of Potent D-Amino Acid Oxidase (DAAO) Inhibitors," J. Med. Chem. 2009, 52, pp. 3576-3585.
English Abstract for BE859 477.
U.S. Appl. No. 14/131,337.
U.S. Appl. No. 13/591,859.
Division of Medicinal Chemistry Scientific Abstracts for the 244th National Meeting and Exposition, Aug. 19-23. 2012, Philadelphia, PA; publication date Jul. 6, 2012 (see Entry MEDI 98).
English Abstract of Aroyan, A. A. at al., Pyrimidine derivatives. XXXVI. Synthesis and IR and mass spectra of 2-(p-alkoxybenzyl)-4,5-dihydroxypyrimidines, Armyanski khimicheskii Zburnal, vol. 27, No. 11, 1974, 963-968; CAS Database Accession No. 1975:140063 CAPLUS.
Hondo. at al., "4-Hydroxypyridazin-3(2H)-one derivatives as novel D-Amino acid oxidase inhibitors," J. Med. Chem. May 9, 2013; 56(9); 3582-92 (web publication date Apr. 8. 2013).
International Search Report, PCT/GB2012/000573, mailed Sep. 10, 2012.
international Search Report and Written Opinion, PCT/GB2012/000672, mailed Oct. 1, 2012.
Office Action (Restriction Requirement) dated Jan. 24, 2013, in U.S. Appl. No. 13/591,859.
Office Action dated Sep. 19, 2013, in U.S. Appl. No. 13/591,859.
U.S. Appl. No. 14/240,045, filed Feb. 21, 2014.
U.S. Appl. No. 14/358,162, filed May 14, 2014.
U.S. Appl. No. 14/652,484, filed Jun. 16, 2015.
Office Action (Restriction Requirement) dated Mar. 16, 2015, in U.S. Appl. No. 14/240,045.
Office Action dated Mar. 18, 2015, in U.S. Appl. No. 14/358,162.
Office Action dated May 8, 2015, in U.S. Appl. No. 13/591,859.
R. Bluth, "Pharmacological Characterization of Novel Pyridazines," Phamazie, vol. 36, No. 11, pp. 775-777 (1981).
Y. Feng et al., "Photolytic and Microbial Degradation of 3,5,6-tricholoro-2-pyridinol," Environmental Toxicology and Chemistry, vol. 17, No. 5, pp. 814-819, (1998).
International Search Report for International Patent Application No. PCT/JP2012/079521, dated Jan. 22, 2013.
International Search Report for International Patent Application No. PCT/GB2013/000552, Mar. 20, 2014.
English language abstract of JP 02-028187, filed Jun. 6, 1989.
English language abstract of JP 09-025234, filed Dec. 7, 1995.
English language abstract of JP 62-84082.
English language abstract of JP 2007-517056.
Jordan, V. C., "Tamoxifen: A most unlikely pioneering medicine," Nature Reviews: Drug Discovery, 2, 2003, 205-213.
Sungawa et al., "Synthesis and Antibacterial Activity of Novel Carbapenems with a Catechol or Hydroxypyridone moiety," Journal of Antibiotics (1994), 47(11), 1354-8.
Hackam, et al., "Translation of Research Evidence from Animals to Humans," J. American Medical Association, 296(14), 2006, pp. 1731-1732.
Office Action dated Jun. 12, 2015, in U.S. Appl. No. 14/240,045.
Notice of Allowance dated Jul. 17, 2015, in U.S. Appl. No. 14/358,162.

\* cited by examiner

5- OR 6-SUBSTITUTED 3-HYDROXY-2 (1 H)-PYRIDINONES AS D-AMINO ACID OXIDASE (DAAO) INHIBITORS IN THERAPY OF DISEASES SUCH AS SCHIZOPHRENIA, COGNITIVE DISORDER AND PAIN

This application is a national stage filing under 35 U.S.C. §371 of International Application No. PCT/GB2012/000574 filed on 5 Jul. 2012, which claims priority of Great Britain Patent Application No. 1111704.1, filed on 7 Jul. 2011. The contents of both applications are incorporated herein by reference.

The present invention relates to pyridinone derivatives, processes for their preparation, pharmaceutical compositions containing them and their use in therapy, particularly in the treatment or prevention of conditions having an association with the D-amino acid oxidase enzyme (DAAO).

The hyper-dopaminergic theory has driven schizophrenia drug discovery for decades and has produced notable drugs such as clozapine and olanzapine. Although these medicaments can be highly efficacious against the positive symptoms of schizophrenia and have significantly benefited many patients they are not the complete answer, with fewer or no effects against the negative and cognitive aspects of the disease and with undesired side effect profiles in some cases. Amongst alternative hypotheses the hyper-glutamatergic theory has much merit with the first real evidence coming from the use of PCP (phencyclidine), MK801 or ketamine, direct N-methyl-D-aspartate (NMDA)-receptor antagonists that are able to produce schizophrenia-like symptomatology in healthy human volunteers or exacerbate the clinical signs in schizophrenia patients. However, direct modulation of the NMDA receptor using agonists has not proved successful with excitotoxicity (excessive stimulation by the neurotransmitter) leading to undesirable side effects. An alternative approach is to target the co-agonists required for NMDA receptor activation. These are glycine and serine (D-SER). Attempts to enhance NMDA receptor activity through the use of glycine transporter inhibitors have produced clinical compounds (but no marketed drugs to-date). D-SER is a co-agonist with even greater potency than glycine and so modulation of D-SER may represent an alternative strategy. One way to increase levels of D-SER is to reduce the activity of DAAO, the enzyme which removes it from the synaptic cleft.

DAAO enzyme inhibitors are known in the art. For example, Adage et al., *European Neuropsychopharmacology* 2008, 18, 200-214 have described AS-057278, a small molecule DAAO enzyme inhibitor. Likewise, Sparey et al., *Bioorganic & Medicinal Chemistry Letters*, 2008, 18, 3386-3391 have demonstrated that molecules containing small heterocyclic rings furnished with a carboxylic acid group can inhibit the DAAO enzyme. DAAO inhibitors which avoid the carboxylic acid group have been described by Ferraris et al., *J. Med. Chem.* 2008, 51, 3357-3359 and by Duplantier et al., *J. Med. Chem.* 2009, 52, 3576-3585. A further series of carboxylic acid-containing DAAO enzyme inhibitors from Sepracore are described in WO 2008/089453.

We have now discovered a new class of compounds that are DAAO enzyme inhibitors which have desirable activity profiles. The compounds of this invention have beneficial potency, selectivity and/or pharmacokinetic properties.

In accordance with the present invention, there is therefore provided a compound of formula (I)

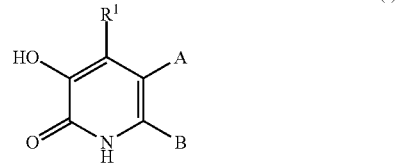

wherein

R$^1$ represents a hydrogen or fluorine atom;

one of A and B represents R$^2$ and the other of A and B represents a group —X—Y—R$^3$;

R$^2$ represents a hydrogen or halogen atom, or a C$_1$-C$_6$ alkyl, C$_3$-C$_6$ cycloalkyl or C$_1$-C$_6$ alkoxy group, each of which may be optionally substituted by at least one substituent selected from hydroxyl, halogen, cyano, nitro, C$_1$-C$_6$ alkyl, C$_3$-C$_6$ cycloalkyl, C$_2$-C$_6$ alkenyl, C$_2$-C$_6$ alkynyl, C$_1$-C$_6$ haloalkyl, C$_1$-C$_6$ hydroxyalkyl, C$_1$-C$_6$ alkoxy, C$_1$-C$_6$ haloalkoxy, C$_1$-C$_6$ alkylcarbonyl, C$_1$-C$_6$ alkylcarbonyloxy, C$_1$-C$_6$ alkoxycarbonyl, —S(O)$_m$R$^4$ and —NR$^5$R$^6$;

m is 0, 1 or 2;

R$^4$ represents a C$_1$-C$_6$ alkyl group;

R$^5$ and R$^6$ each independently represent a hydrogen atom or a C$_1$-C$_6$ alkyl group;

X and Y each independently represent a bond, an oxygen atom or a group —C(O)—, —S(O)$_n$, —C(O)NR$^7$, —S(O)$_2$NR$^7$, —NR$^7$,

or —CR$^7$R$^8$—, provided that X and Y cannot both simultaneously represent a bond and provided that if X and Y are both other than a bond, then at least one of X and Y represents —CR$^7$R$^8$—;

n is 0, 1 or 2;

each R$^7$ independently represents a hydrogen atom or a C$_1$-C$_6$ alkyl group;

each R$^8$ independently represents a hydrogen atom, a C$_1$-C$_6$ alkyl group or =CH—;

R$^3$ represents a 3- to 10-membered saturated or unsaturated carbocyclic or heterocyclic ring system, the ring system itself being optionally substituted by at least one substituent selected from halogen, hydroxyl, cyano, oxo, C$_1$-C$_6$ alkyl, C$_2$-C$_6$ alkenyl, C$_1$-C$_6$ haloalkyl, C$_1$-C$_6$ hydroxyalkyl, C$_1$-C$_6$ alkoxy, C$_1$-C$_6$ haloalkoxy, C$_1$-C$_6$ alkylthio, C$_1$-C$_6$ alkylsulphinyl, C$_1$-C$_6$ alkylsulphonyl, C$_1$-C$_6$ alkylcarbonyl, C$_1$-C$_6$ alkylcarbonyloxy, C$_1$-C$_6$ alkoxycarbonyl, amino (—NH$_2$), —CON(R$^9$)$_2$, C$_1$-C$_6$ alkylamino, di-(C$_1$-C$_6$ alkyl)amino, C$_3$-C$_6$ cycloalkyl, C$_3$-C$_6$ cycloalkyloxy, C$_3$-C$_6$ cycloalkylmethyl, —[O]$_p$—(CH$_2$)$_q$—O—R$^{10}$ and a 4- to 6-membered saturated or unsaturated heterocyclic ring (optionally substituted with at least one substituent selected from C$_1$-C$_4$ alkyl and C$_1$-C$_4$ alkoxy);

each $R^9$ independently represents a hydrogen atom or a $C_1$-$C_6$ alkyl group;

p is 0 or 1;

q is 1, 2, 3 or 4; and $R^{10}$ represents a $C_1$-$C_6$ alkyl group;

or a pharmaceutically acceptable salt thereof.

In the context of the present specification, unless otherwise stated, an alkyl, alkenyl or alkynyl substituent group or an alkyl, alkenyl or alkynyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl.

Similarly, an alkylene group/moiety may be linear or branched. Examples of $C_1$-$C_6$ alkylene groups/moieties include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene.

A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl.

A $C_1$-$C_6$ hydroxyalkyl substituent group/moiety will comprise at least one hydroxyl group, e.g. one, two, three or four hydroxyl groups, examples of which include $CH_2OH$, —$CH_2CH_2OH$, —$CH_2CH_2CH_2OH$, —$CH(OH)CH_2OH$, —$CH(CH_3)OH$ and —$CH(CH_2OH)_2$.

The alkyl groups in a di-$C_1$-$C_6$ alkylamino group/moiety may be the same as, or different from, one another.

In the definition of $R^3$, the saturated or unsaturated 3- to 10-membered carbocyclic or heterocyclic ring system may have alicyclic or aromatic properties as too will the 4- to 6-membered saturated or unsaturated heterocyclic ring substituent. An unsaturated ring system will be partially or fully unsaturated.

For the avoidance of doubt, when $R^3$ represents a 3- to 10-membered saturated or unsaturated carbocyclic or heterocyclic ring system, then it should be understood that the invention does not encompass any unstable ring structures or any O-O, O—S or S—S bonds and that a substituent, if present, may be attached to any suitable ring atom. Similar comments apply with respect to the optional 4- to 6-membered saturated or unsaturated heterocyclic ring substituent on the $R^3$ ring system.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In an embodiment of the invention, $R^1$ represents a hydrogen atom.

In another embodiment, A represents a group —X—Y—$R^3$ and B represents $R^2$.

$R^2$ represents a hydrogen or halogen (e.g. fluorine, chlorine or bromine) atom, or a $C_1$-$C_6$, or $C_1$-$C_4$, or $C_1$-$C_2$ alkyl, $C_3$-$C_6$ or $C_5$-$C_6$ cycloalkyl, or $C_1$-$C_6$, or $C_1$-$C_4$, or $C_1$-$C_2$ alkoxy group, each of which may be optionally substituted by at least one substituent (e.g. one, two, three or four substituents independently) selected from hydroxyl, halogen (e.g. fluorine, chlorine or bromine), cyano, nitro, $C_1$-$C_6$, or $C_1$-$C_4$, or $C_1$-$C_2$ alkyl, $C_3$-$C_6$ or $C_5$-$C_6$ cycloalkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, —$S(O)_mR^4$ and —$NR^5R^6$.

In one embodiment, $R^2$ represents a hydrogen or halogen (e.g. fluorine, chlorine or bromine) atom, or a $C_1$-$C_4$ alkyl, $C_3$-$C_6$ cycloalkyl, or $C_1$-$C_4$ alkoxy group, each of which may be optionally substituted by one, two, three or four substituents independently selected from hydroxyl, halogen (e.g. fluorine, chlorine or bromine), cyano, nitro, $C_1$-$C_6$, or $C_1$-$C_4$, or $C_1$-$C_2$ alkyl, $C_3$-$C_6$ or $C_5$-$C_6$ cycloalkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, —$S(O)_mR^4$ and —$NR^5R^6$.

In another embodiment, $R^2$ represents a hydrogen or halogen (e.g. fluorine, chlorine or bromine) atom, or a $C_1$-$C_4$ alkyl or $C_3$-$C_6$ cycloalkyl group, each of which may be optionally substituted by one, two, three or four substituents independently selected from hydroxyl, fluorine, chlorine, cyano, nitro, $C_1$-$C_4$, or $C_1$-$C_3$, or $C_1$-$C_2$ alkyl, $C_3$-$C_6$ or $C_5$-$C_6$ cycloalkyl, $C_1$-$C_4$ or $C_1$-$C_2$ haloalkyl, $C_1$-$C_4$ or $C_1$-$C_2$ alkoxy, $C_1$-$C_4$ or $C_1$-$C_2$ alkylcarbonyl, $C_1$-$C_4$ or $C_1$-$C_2$ alkylcarbonyloxy, $C_1$-$C_4$ or $C_1$-$C_2$ alkoxycarbonyl, —$S(O)_mR^4$ and —$NR^5R^6$.

In a further embodiment, $R^2$ represents a hydrogen atom or a $C_1$-$C_4$ alkyl or $C_3$-$C_5$ cycloalkyl group, particularly a hydrogen atom.

$R^4$ represents a $C_1$-$C_6$ alkyl group and $R^5$ and $R^6$ each independently represent a hydrogen atom or a $C_1$-$C_6$ alkyl group. Examples of alkyl groups are described above and include methyl, ethyl, iso-propyl, n-propyl and n-butyl.

In one particular aspect, $R^4$, $R^5$ and $R^6$ each independently represent a methyl or ethyl group.

X and Y each independently represent a bond, an oxygen atom or a group —C(O)—, —S(O)$_n$—, —C(O)NR$^7$, —S(O)$_2$NR$^7$, —NR$^7$,

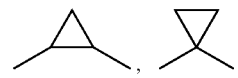

or —CR$^7R^8$—, provided that X and Y cannot both simultaneously represent a bond and provided that if X and Y are both other than a bond, then at least one of X and Y represents —CR$^7$, R$^8$—.

Each $R^7$ independently represents a hydrogen atom or a $C_1$-$C_6$, or $C_1$-$C_4$, or $C_1$-$C_2$ alkyl, preferably methyl, group.

Each $R^8$ independently represents a hydrogen atom, a $C_1$-$C_6$, or $C_1$-$C_4$, or $C_1$-$C_2$ alkyl, preferably methyl, group, or a group =CH— such that —CR$^7R^8$— represents an alkenylene moiety, —CR$^7$=CH— or CH=CR$^7$—.

In one embodiment of the invention, X represents a bond, an oxygen atom or a group —C(O), —S(O)$_n$, —C(O)NR$^7$, —S(O)$_2$NR$^7$, —NR$^7$,

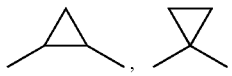

or —CR$^7$R$^8$—, and Y represents a bond or —CR$^7$R$^8$—, subject to the above provisos.

In another embodiment of the invention, X represents —CR$^7$R$^8$— and Y represents a bond, an oxygen atom or a group C(O), —S(O)$_n$, —C(O)NR$^7$, —S(O)$_2$NR$^7$, —NR$^7$,

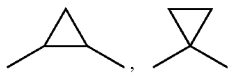

or —CR$^7$R$^8$—, subject to the above provisos.

In a further embodiment, X represents a group —S(O)$_n$ or —CHR$^7$ and Y represents a group —CHR$^7$.

In an embodiment of the invention, X and Y each independently represent a bond, an oxygen atom or a group —C(O), —S(O)$_n$, —C(O)NR$^7$, —S(O)$_2$NR$^7$, —NR$^7$,

or —CR$^7$R$^8$—, provided that X and Y cannot both simultaneously represent a bond and provided that if X and Y are both other than a bond, then at least one of X and Y represents —CR$^7$R$^8$— and further provided that X and Y cannot both simultaneously represent —CR$^7$R$^8$— and if one of X and Y represents —CR$^7$R$^8$—, then the other of X and Y does not represent a bond.

Specific examples of combinations of X and Y are shown in the following table:

| X | Y |
|---|---|
| S | CH$_2$ |
| CH$_2$ | S |
| CH$_2$ | CH$_2$ |
| S | CH(CH$_3$) |
| SO$_2$ | CH$_2$ |
| CH$_2$ | SO$_2$ |
| O | CH$_2$ |
| O | CH(CH$_3$) |
| C(O) | CH$_2$ |
| C(O)NH | CH$_2$ |
| S(O)$_2$NH | CH$_2$ |
| CH$_2$ | CH(CH$_3$) |
| CH(CH$_3$) | CH$_2$ |
| CH$_2$ | C(CH$_3$)$_2$ |
| C(CH$_3$)$_2$ | CH$_2$ |
| —CH=CH— | bond |
| bond | —CH=CH— |

Particularly advantageous combinations of X and Y include:

| X | Y |
|---|---|
| S | CH$_2$ |
| CH$_2$ | CH$_2$ |
| S | CH(CH$_3$) |
| SO$_2$ | CH$_2$ |

Each R$^9$ independently represents a hydrogen atom or C$_1$-C$_6$, or C$_1$-C$_4$, or C$_1$-C$_2$ alkyl group. Examples of alkyl groups are described above and include methyl, ethyl, isopropyl, n-propyl and n-butyl.

R$^{10}$ represents a C$_1$-C$_6$, or C$_1$-C$_4$, or C$_1$-C$_2$ alkyl group, examples of which have been previously described.

According to one aspect of the invention, R$^3$ may represent a 3- to 10-membered (e.g. 3-, 4-, 5- or 6- to 7-, 8-, 9- or 10-membered) saturated or unsaturated carbocyclic or heterocyclic ring system which is optionally substituted by at least one substituent (e.g. one, two, three or four substituents independently) selected from halogen (e.g. fluorine, chlorine or bromine), hydroxyl, cyano, oxo, C$_1$-C$_6$, or C$_1$-C$_4$, or C$_1$-C$_2$ alkyl, C$_2$-C$_6$ or C$_2$-C$_4$ alkenyl, C$_1$-C$_6$, or C$_1$-C$_4$, or C$_1$-C$_2$ haloalkyl, C$_1$-C$_6$, or C$_1$-C$_4$, or C$_1$-C$_2$ hydroxyalkyl, C$_1$-C$_6$, or C$_1$-C$_4$, or C$_1$-C$_2$ alkoxy, C$_1$-C$_6$, or C$_1$-C$_4$, or C$_1$-C$_2$ haloalkoxy, C$_1$-C$_6$, or C$_1$-C$_4$, or C$_1$-C$_2$ alkylthio, C$_1$-C$_6$, or C$_1$-C$_4$, or C$_1$-C$_2$ alkylsulphinyl, C$_1$-C$_6$, or C$_1$-C$_4$, or C$_1$-C$_2$ alkylsulphonyl, C$_1$-C$_6$, or C$_1$-C$_4$, or C$_1$-C$_2$ alkylcarbonyl, C$_1$-C$_6$, or C$_1$-C$_4$, or C$_1$-C$_2$ alkylcarbonyloxy, C$_1$-C$_6$, or C$_1$-C$_4$, or C$_1$-C$_2$ alkoxycarbonyl, amino, —CON(R$^9$)$_2$, C$_1$-C$_6$, or C$_1$-C$_4$, or C$_1$-C$_2$ alkylamino, di-(C$_1$-C$_6$, or C$_1$-C$_4$, or C$_1$-C$_2$ alkyl)amino, C$_3$-C$_6$ or C$_3$-C$_5$ cycloalkyl, C$_3$-C$_6$ or C$_3$-C$_5$ cycloalkyloxy, C$_3$-C$_6$ or C$_3$-C$_5$ cycloalkylmethyl, —[O]$_p$—(CH$_2$)$_q$—O—R$^{10}$ and a 4- to 6-membered saturated or unsaturated heterocyclic ring (optionally substituted with at least one substituent, e.g. one, two or three substituents independently, selected from C$_1$-C$_4$ alkyl such as methyl or ethyl and C$_1$-C$_4$ alkoxy such as methoxy or ethoxy).

The heterocyclic ring system will comprise at least one ring heteroatom (e.g. one, two, three or four ring heteroatoms independently) selected from nitrogen, sulphur and oxygen.

Examples of saturated or unsaturated 3- to 10-membered carbocyclic or heterocyclic ring systems that may be used, which may be monocyclic or polycyclic (e.g. bicyclic) in which the two or more rings are fused, include one or more (in any combination) of cyclopropyl, cyclobutyl, cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, oxadiazolyl (e.g. 1,2,4-oxadiazolyl), tetrahydrofuranyl, diazabicyclo[2.2.1]hept-2-yl, naphthyl, benzofuranyl, benzothienyl, benzodioxolyl, quinolinyl, oxazolyl, thiadiazolyl (e.g. 1,2,3-thiadiazolyl), 2,3-dihydrobenzofuranyl, tetrahydropyranyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, indolyl, imidazolyl, pyrimidinyl, benzimidazolyl, triazolyl, tetrazolyl, and pyridinyl.

Preferred ring systems include phenyl, pyridinyl, oxazolyl, pyrazinyl, cyclopropyl, cyclopentyl, cyclohexyl, tetrahydropyranyl, 2,3-dihydrobenzofuranyl, pyrimidinyl, imidazo[1,2-a]pyridinyl, pyrazolyl and piperidinyl.

Advantageously, the ring system is phenyl, pyridinyl, oxazolyl or pyrazinyl.

The 4- to 6-membered saturated or unsaturated heterocyclic ring substituent will comprise at least one ring heteroatom (e.g. one, two, three or four ring heteroatoms independently) selected from nitrogen, sulphur and oxygen. Preferably the ring heteroatoms are selected from nitrogen and oxygen. Examples of such ring substituents include azetidinyl, pyrrolidinyl and oxadiazolyl such as 1,2,4-oxadiazolyl.

In one embodiment of the invention, $R^3$ represents a 3-, 4- or 5- to 6-, 7-, 8- or 9-membered, e.g. 5- to 9-membered, saturated or unsaturated carbocyclic or heterocyclic ring system optionally substituted by at least one substituent (e.g. one, two, three or four substituents independently) selected from halogen (e.g. fluorine, chlorine or bromine), hydroxyl, cyano, oxo, $C_1$-$C_4$ alkyl (e.g. methyl or ethyl), $C_2$-$C_4$ alkenyl (e.g. ethenyl), $C_1$-$C_2$ haloalkyl (e.g. trifluoromethyl), $C_1$-$C_2$ hydroxyalkyl (e.g. hydroxymethyl), $C_1$-$C_4$ alkoxy (e.g. methoxy or ethoxy), $C_1$-$C_2$ haloalkoxy (e.g. trifluoromethoxy), $C_1$-$C_4$ alkylthio (e.g. methylthio or ethylthio), $C_1$-$C_4$ alkylsulphinyl (e.g. methylsulphinyl or ethylsulphinyl), $C_1$-$C_4$ alkylsulphonyl (e.g. methylsulphonyl or ethylsulphonyl), $C_1$-$C_4$ alkylcarbonyl (e.g. methylcarbonyl or ethylcarbonyl), $C_1$-$C_4$ alkylcarbonyloxy (e.g. methylcarbonyloxy), $C_1$-$C_4$ alkoxycarbonyl (e.g. methoxycarbonyl), amino, —CON($R^9$)$_2$, $C_1$-$C_4$ alkylamino (e.g. methylamino or ethylamino), di-($C_1$-$C_4$ alkyl)amino (e.g. dimethylamino), $C_3$-$C_5$ cycloalkyl, $C_3$-$C_5$ cycloalkyloxy, $C_3$-$C_5$ cycloalkylmethyl, —[O]$_p$—(CH$_2$)$_q$—O—$R^{10}$ and a 4- to 6-membered saturated or unsaturated heterocyclic ring optionally substituted by methyl or methoxy.

In another embodiment of the invention, $R^3$ represents a 5- or 6-membered unsaturated carbocyclic or heterocyclic ring system, the heterocyclic ring system comprising one or two ring heteroatoms independently selected from nitrogen and oxygen, wherein the carbocyclic or heterocyclic ring system is optionally substituted by one, two, three or four substituents independently selected from fluorine, chlorine, bromine, hydroxyl, cyano, oxo, $C_1$-$C_4$ alkyl (e.g. methyl or ethyl), $C_2$-$C_4$ alkenyl (e.g. ethenyl), $C_1$-$C_2$ haloalkyl (e.g. trifluoromethyl), $C_1$-$C_2$ hydroxyalkyl (e.g. hydroxymethyl), $C_1$-$C_4$ alkoxy (e.g. methoxy or ethoxy), $C_1$-$C_2$ haloalkoxy (e.g. trifluoromethoxy), $C_1$-$C_4$ alkylthio (e.g. methylthio or ethylthio), $C_1$-$C_4$ alkylsulphinyl (e.g. methylsulphinyl or ethylsulphinyl), $C_1$-$C_4$ alkylsulphonyl (e.g. methylsulphonyl or ethylsulphonyl), $C_1$-$C_4$ alkylcarbonyl (e.g. methylcarbonyl or ethylcarbonyl), $C_1$-$C_4$ alkylcarbonyloxy (e.g. methylcarbonyloxy), $C_1$-$C_4$ alkoxycarbonyl (e.g. methoxycarbonyl), amino, carboxamido (—CONH$_2$), $C_1$-$C_4$ alkylamino (e.g. methylamino or ethylamino), di-($C_1$-$C_4$ alkyl)amino (e.g. dimethylamino), $C_3$-$C_4$ cycloalkyl, $C_3$-$C_4$ cycloalkyloxy, $C_3$-$C_4$ cycloalkylmethyl, —[O]$_p$—(CH$_2$)$_q$—O—$R^{10}$ and a 4- to 5-membered saturated or unsaturated heterocyclic ring, preferably containing at least one ring nitrogen atom, optionally substituted by methyl or methoxy.

In still another embodiment, $R^3$ represents a 5- or 6-membered unsaturated carbocyclic or heterocyclic ring system such as phenyl, pyridinyl, oxazolyl and pyrazinyl, which ring system is optionally substituted by at least one substituent (e.g. one, two, three or four, preferably one or two, substituents independently) selected from fluorine, chlorine, methyl, ethyl, trifluoromethyl and methoxy.

In a preferred embodiment of the invention,
$R^1$ represents a hydrogen atom;
one of A and B represents $R^2$ and the other of A and B represents a group —X—Y—$R^3$;
$R^2$ represents a hydrogen atom;
X represents a group —S(O)$_n$ or —CHR$^7$ and Y represents a group —CHR$^7$;
n is 0, 1 or 2;
each $R^7$ independently represents a hydrogen atom or a methyl group; and
$R^3$ represents a 5- or 6-membered unsaturated carbocyclic or heterocyclic ring system which ring system is optionally substituted by at least one substituent selected from fluorine, chlorine, methyl, ethyl, trifluoromethyl and methoxy.

Examples of compounds of the invention include:
5-(Benzylsulfanyl)-3-hydroxypyridin-2(1H)-one,
5-[(4-Chlorobenzyl)sulfanyl]-3-hydroxypyridin-2(1H)-one,
3-Hydroxy-5-[(4-methylbenzyl)sulfanyl]pyridin-2(1H)-one,
3-Hydroxy-5-[(3-methylbenzyl)sulfanyl]pyridin-2(1H)-one,
5[(3-Chlorobenzyl)sulfanyl]-3-hydroxypyridin-2(1H)-one,
3-Hydroxy-5-[(1-phenylethyl)sulfanyl]pyridin-2(1H)-one,
5-[(2-Chlorobenzyl)sulfanyl]-3-hydroxypyridin-2(1H)-one,
3-Hydroxy-5-{[3-(trifluoromethyl)benzyl]sulfanyl}pyridin-2(1H)-one,
3-Hydroxy-5-[(2-methylbenzyl)sulfanyl]pyridin-2(1H)-one,
5-[(3-Chloro-5-fluorobenzyl)sulfanyl]-3-hydroxypyridin-2(1H)-one,
5-[(4-Fluorobenzyl)sulfanyl]-3-hydroxypyridin-2(1H)-one,
5-[(4-Ethylbenzyl)sulfanyl]-3-hydroxypyridin-2(1H)-one,
3-Hydroxy-5-({[6-(trifluoromethyl)pyridin-3-yl]methyl}-sulfanyl)pyridin-2(1H)-one,
3-Hydroxy-5-{[(3-methylpyridin-2-yl)methyl]sulfanyl}pyridin-2(1H)-one,
5-{[(3,5-Dimethyl-1,2-oxazol-4-yl)methyl]sulfanyl}-3-hydroxypyridin-2(1H)-one,
3-Hydroxy-5-{[(2-methyl-1,3-oxazol-4-yl)methyl]sulfanyl}-pyridin-2(1H)-one,
3-Hydroxy-5-[(pyridin-2-ylmethyl)sulfanyl]pyridin-2(1H)-one,
3-Hydroxy-5-[(pyridin-4-ylmethyl)sulfanyl]pyridin-2(1H)-one,
5-{[(5-Chloropyridin-2-yl)methyl]sulfanyl}-3-hydroxypyridin-2(1H)-one,
5-[(3,4-Difluorobenzyl)sulfanyl]-3-hydroxypyridin-2(1H)-one,
3-Hydroxy-5-[(4-methoxybenzyl)sulfanyl]pyridin-2(1H)-one,
3-Hydroxy-5-[(pyridin-3-ylmethyl)sulfanyl]pyridin-2(1H)-one,
3-Hydroxy-5-{[(5-methylpyridin-2-yl)methyl]sulfanyl}pyridin-2(1H)-one,
3-Hydroxy-5-[(pyrazin-2-ylmethyl)sulfanyl]pyridin-2(1H)-one,
3-Hydroxy-5-{[(6-methoxypyridin-3-yl)methyl]-sulfanyl}-pyridin-2(1H)-one,
3-Hydroxy-5-(2-methylphenethyl)pyridin-2(1H)-one,
3-Hydroxy-5-(2-phenylethyl)pyridin-2(1H)-one,
3-Hydroxy-5-[2-(3-methylphenyl)ethyl]pyridin-2(1H)-one,
3-Hydroxy-5-[2-(4-methylphenyl)ethyl]pyridin-2(1H)-one,
5-[2-(4-Fluorophenyl)ethyl]-3-hydroxypyridin-2(1H)-one,
5-[2-(3-Fluorophenyl)ethyl]-3-hydroxypyridin-2(1H)-one,
5-[2-(2-Fluorophenyl)ethyl]-3-hydroxypyridin-2(1H)-one,
5-(Benzylsulfonyl)-3-hydroxypyridin-2(1H)-one,
5-[(3-Fluorobenzyl)sulfanyl]-3-hydroxypyridin-2(1H)-one,
6-(benzylsulfanyl)-3-hydroxypyridin-2(1H)-one,
and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises (i) when X represents a sulphur atom or when X is a bond and Y represents a sulphur atom, reacting a compound of formula (IIa) or (IIb)

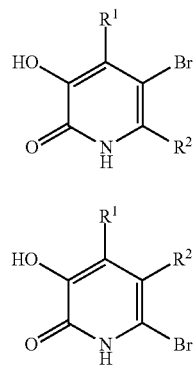

in which $R^1$ and $R^2$ are as defined in formula (I), with a compound of formula (III), $HS—[Y]_t—R^3$, where t is 0 or 1 and Y and $R^3$ are as defined in formula (I); or (ii) when X represents SO or when X is a bond and Y represents SO, oxidising a compound of formula (IVa) or (IVb)

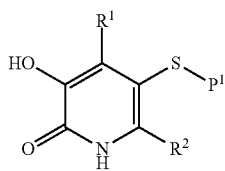

in which $P^1$ represents a protecting group (e.g. methyl proprionate) and $R^1$ and $R^2$ are as defined in formula (I) with a suitable oxidising agent, followed by reaction with a compound of formula (V), $L^1-[Y]_w—R^3$, where w is 0 or 1, $L^1$ represents a leaving group (e.g. halogen) and Y and $R^3$ are as defined in formula (I); or (iii) when X represents $SO_2$ or when X is a bond and Y represents $SO_2$, oxidising a compound of formula (IVa) or (IVb) as defined in (ii) above with a suitable oxidising agent, followed by reaction with a compound of formula (V) as defined in (ii) above; or (iv) when X represents an oxygen atom or when X is a bond and Y represents an oxygen atom, reacting a compound of formula (IIa) or (IIb) as defined in (i) above, with a compound of formula (VI), $HO—[Y]_z—R^3$, where z is 0 or 1 and Y and $R^3$ are as defined in formula (I); or (v) when X represents C(O) or when X is a bond and Y represents C(O), reacting a compound of formula (IIa) or (IIb) as defined in (i) above with carbon dioxide, followed by addition of an activating agent and reaction with a compound of formula (Va), $M-[Y]_w—R^3$, where M is Li or $MgR^{20}$, $R^{20}$ represents a halogen atom and w, Y and $R^3$ are as defined in formula (V) in (ii) above; or (vi) when X represents $—C(O)NR^7$ or when X is a bond and Y represents $—C(O)NR^7$, reacting a compound of formula (VIIa) or (VIIb)

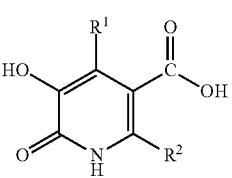

in which $R^1$ and $R^2$ are as defined in formula (I), with a compound of formula (VIII), $R^7HN—[Y]_g—R^3$, where g is 0 or 1 and Y, $R^3$ and $R^7$ are as defined in formula (I); or (vii) when X represents $—S(O)_2NR^7$ or when X is a bond and Y represents $—S(O)_2NR^7$, reacting a compound of formula (IIa) or (IIb) as defined in (i) above with sulphur dioxide, followed by addition of an oxidising-chlorinating agent and then reaction with a compound of formula (VIII) as defined in (vi) above; or (viii) when X represents $—NR^7$ or when X is a bond and Y represents $—NR^7$, reacting a compound of formula (IIa) or (IIb) as defined in (i) above, with a compound of formula (VIII) as defined in (vi) above; or (ix) when X represents $—CR^7R^8—$ or when X is a bond and Y represents $—CR^7R^8—$ and $R^7$ and $R^8$ each independently represent a $C_1$-$C_6$ alkyl group, reacting a compound of formula (IIa) or (IIb) as defined in (i) above with a compound of formula (IX), $L^2-CR^{7'}R^{8'}—[Y]_h—R^3$, where h is 0 or 1, $L^2$ represents a leaving group (e.g. halogen), $R^{7'}$ and $R^{8'}$ each independently represent a $C_1$-$C_6$ alkyl group and Y and $R^3$ are as defined in formula (I); or (x) when X represents $—CR^7R^8—$ or when X is a bond and Y represents $—CR^7R^8—$ and $R^7$ and $R^8$ each independently represent a hydrogen atom or a $C_1$-$C_6$ alkyl group but do not both simultaneously represent a $C_1$-$C_6$ alkyl group, reacting a compound of formula (IIa) or (IIb) as defined in (i) above with a compound of formula (IXa), $R^7C(O)—[Y]_h—R^3$, wherein h, Y, and $R^3$ are as defined in formula (IX) in (ix) above and $R^7$ is as defined in formula (I) above, followed by a hydrogenation reaction; or (xi) when X and Y each represent —CHR⁷, hydrogenating a compound of formula (Xa) or (Xb)

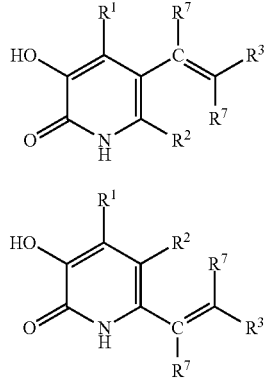

(Xa)

(Xb)

wherein $R^1$, $R^2$, $R^3$ and $R^7$ are as defined in formula (I); or (xii) when X represents —CR⁷R⁸— or when X is a bond and Y represents —CR⁷R⁸— and R⁸ is =CH, reacting a compound of formula (XIa) or (XIb)

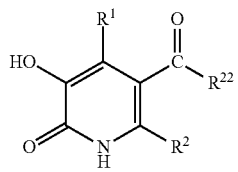

(XIa)

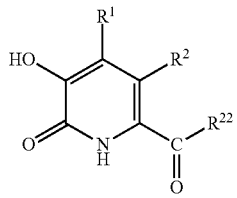

(XIb)

wherein $R^{22}$ represents a hydrogen atom or a $C_1$-$C_6$ alkyl group and $R^1$ and $R^2$ are as defined in formula (I), with a compound of formula (IXb), $R^{24}$—CH($R^{26}$)—$[Y]_h$—$R^3$, wherein $R^{24}$ represents a phosphonate moiety (e.g. —P(=O)(OR)₂ where R is an alkyl group such as ethyl), $R^{26}$ represents a hydrogen atom or a $C_1$-$C_6$ alkyl group and h, Y and $R^3$ are as defined in formula (IX) in (ix) above; or (xiii) when X represents a group

or when X is a bond and Y represents a group

reacting a compound of formula (XIIa) or (XIIb)

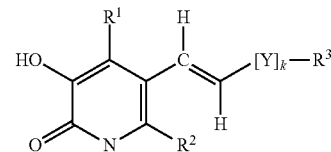

(XIIa)

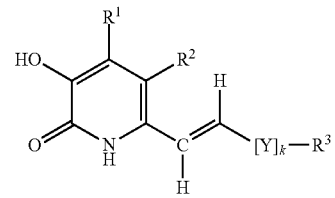

(XIIb)

where k is 0 or 1 and Y, $R^1$, $R^2$ and $R^3$ are as defined in formula (I), with diiodomethane and zinc-copper couple; or (xiv) when X represents a group

or when X is a bond and Y represents a group

reacting a compound of formula (XIIIa) or (XIIIb)

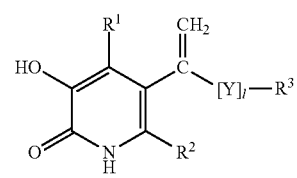

(XIIIa)

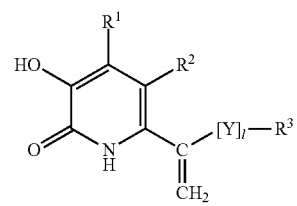

(XIIIb)

where l is 0 or 1 and Y, $R^1$, $R^2$ and $R^3$ are as defined in formula (I), with diiodomethane and zinc-copper couple;

and optionally thereafter carrying out one or more of the following procedures:
    converting a compound of formula (I) into another compound of formula (I)
    removing any protecting groups
    forming a pharmaceutically acceptable salt.

Process (i) may conveniently be carried out in an organic solvent such as toluene in the presence of a palladium catalyst, e.g. tris(dibenzylideneacetone)dipalladium(0) (Pd₂(DBA)₃) and an organophosphorous compound such as 4,5-bis(diphenylphospliino)-9,9-dimethylxanthene (Xantphos).

Processes (ii) and (iii) may conveniently be carried out in an organic solvent such as dichloromethane using a suitable amount of an oxidising agent such as meta-chloroperoxybenzoic acid.

Process (iv) may conveniently be carried out in an organic solvent such as toluene in the presence of a copper (I) iodide catalyst at elevated temperature (e.g. 30° C. to 150° C.).

The first step of process (v) may conveniently be carried out in an organic solvent such as diethyl ether at low temperature (e.g. −78° C.) in the presence of a reagent such as butyllithium. A suitable activating agent to use in the second step would be a compound such as N,O-dimethylhydroxylamine hydrochloride which is commercially available, e.g. from the Sigma-Aldrich Corporation, to form a 'Weinreb amide' which is then reacted with the compound of formula (Va) to form the appropriate compound of formula (I).

Process (vi) may conveniently be carried out in an organic solvent using a suitable amide coupling reagent. Various amide coupling reagents are known in the art such as dicyclohexylcarbodiimide (DCC), diisopropylcarbodiimide (DIC), O-(benzotriazol-1-yl)-N,N,N',N'-tetramethyluronium hexafluorophosphate (HBTU) and O-(benzotriazol-1-yl)-N,N,N',N'-tetramethyluronium tetrafluoroborate (TBTU).

The first step of process (vii) may conveniently be carried out in an organic solvent such as diethyl ether at low temperature (e.g. −78° C.) in the presence of a reagent such as isopropylmagnesium chloride. A suitable oxidising-chlorinating agent to use in the second step would be sulphuryl chloride and the subsequent reaction with a compound of formula (VIII) may be carried out in accordance with known sulphonamide coupling procedures in the art.

The amination reaction in process (viii) may conveniently be carried out in an organic solvent such as toluene in the presence of (1) a palladium catalyst such as tris(dibenzylideneacetone)dipalladium(0) ($Pd_2(DBA)_3$), (2) a base such as sodium t-butoxide and (3) an organophosphorous compound such as 4,5-bis(diphenylphosphino)-9,9-dimethylxanthene (Xantphos).

Processes (ix) and (x) may conveniently be carried out in an organic solvent such as diethyl ether at low temperature (e.g. −78° C.) in the presence of a reagent such as butyllithium.

The hydrogenation reaction in process (x) and process (xi) may be carried out according to techniques known in the art, e.g. in the presence of an organic solvent such as ethanol using hydrogen gas and a palladium on carbon catalyst, under acid catalysed conditions as required.

Process (xii) is analogous to a Horner-Wadsworth-Emmons reaction as known, for example, from Wadsworth, W. Org. React. 1977, 25, 73. Suitable reaction conditions for carrying out this type of reaction are known in the art.

Processes (xiii) and (xiv) are analogous to the Simmons-Smith cyclopropanation reaction of alkenes, for example, as described by Howard H. Simmons, Ronald D. Smith (1959) "A New Synthesis of Cyclopropanes" J. Am. Chem. Soc. 81 (16): 4256-4264.

Compounds of formula (IVa) or (IVb) in which $P^1$ represents a protecting group such as —$CH_2CH_2C(O)OCH_3$ may be prepared by reacting a compound of formula (IIa) or (IIb) as defined above with methyl 3-sulfanylpropanoate.

Compounds of formula (VIIa) or (VIIb) may be prepared by reacting a compound of formula (IIa) or (IIb) as defined above with carbon dioxide in an organic solvent such as diethyl ether at low temperature (e.g. −78° C.) in the presence of a reagent such as butyllithium.

Compounds of formula (Xa) or (Xb) may be prepared by processes analogous to process (xii) above.

Compounds of formula (XIa) or (XIb) may be prepared by reacting a compound of formula (IIa) or (IIb) as defined above with dimethylformamide in an organic solvent such as diethyl ether at low temperature (e.g. −78° C.) in the presence of a reagent such as butyllithium, optionally followed by an alkylation reaction.

Compounds of (XIIa) or (XIIb) may be prepared by processes analogous to those used for the preparation of compounds of formula (Xa) or (Xb).

Compounds of formula (XIIIa) or (XIIIb) may be prepared according to the following reaction scheme:

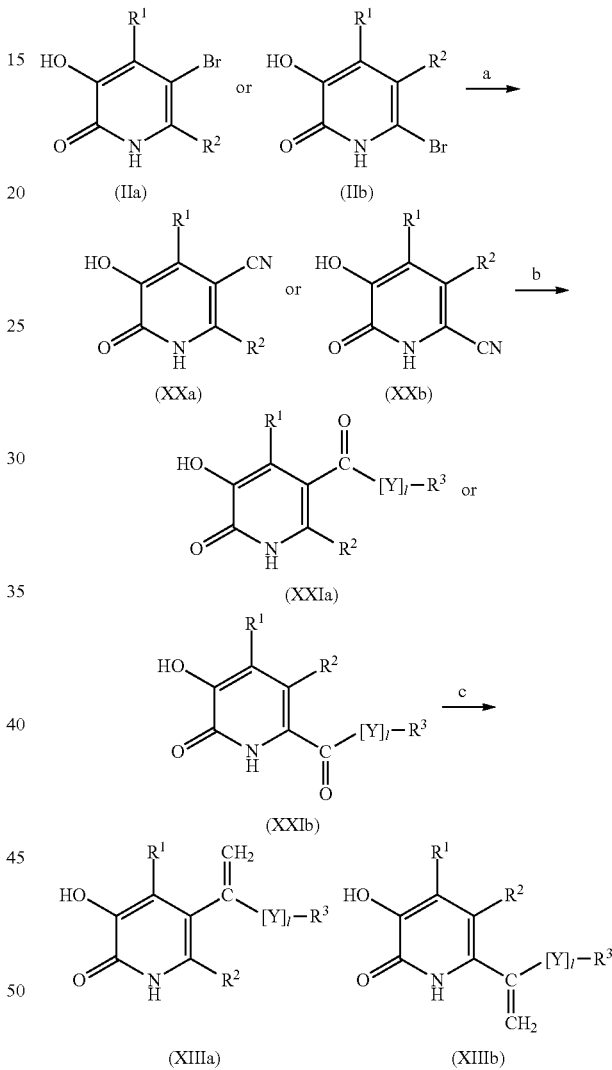

Step a is carried out using, for example, copper cyanide.

Step b is carried out using a Grignard reagent of formula $R^3$—[Y]$_l$—MgBr where l, Y and $R^3$ are as defined in formula (XIIIa) or (XIIIb).

Step c is carried out using Tebbe reagent solution (bis (cyclopentadienyl)-μ-chloro-(dimethylaluminum)-μ-methylenetitanium).

Compounds of formulae (IIa), (IIb), (III), (V), (Va), (VI), (VIII), (IX), (IXa) and (IXb) are either commercially available, are well known in the literature or may be prepared using known techniques.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as D-amino acid oxidase enzyme (DAAO) inhibitors, and thus may be used in the treatment of schizophrenia and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder and disruptive behaviour disorders), pain (e.g. neuropathic pain) and neurodegenerative disorders (e.g. Parkinson's or Alzheimer's disease).

Thus, the present invention provides a compound of formula (I) or a pharmaceutically acceptable salt thereof as hereinbefore defined for use in therapy, in particular for the treatment of conditions whose development or symptoms are linked to DAAO enzyme activity.

The present invention also provides the use of a compound of formula (I) or a pharmaceutically acceptable salt thereof as hereinbefore defined for the preparation of a medicament for the treatment of conditions whose development or symptoms are linked to DAAO enzyme activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic, testing or screening to be particularly susceptible to developing the disorder or condition or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning) and also pain (such as neuropathic pain).

The invention also provides a method of treating at least one symptom or condition associated with schizophrenia, schizophreniform disorder, schizoaffective disorder and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder, autistic spectrum disorders and disruptive behaviour disorders), pain (e.g. neuropathic pain) and neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill. Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant such as that described in Ph. Helv. or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(v) anticonvulsants including, for example, carbamazepine, valproate, lamotrigine, and gabapentin, and equivalents and pharmaceutically active isomer(s) and/or metabolite(s) thereof;
(vi) Alzheimer's therapies including, for example, donepezil, memantine, tacrine, and equivalents and pharmaceutically active isomer(s) and/or metabolite(s) thereof;
(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;
(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;
(ix) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;
(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;
(xi) neuropathic pain therapies including, for example, gabapentin, lidoderm, and pregablin, and equivalents and pharmaceutically active isomer(s) and/or metabolite(s) thereof;
(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;
(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and Zolpidem, and equivalents and pharmaceutically active isomer(s) and/or metabolite(s) thereof;
(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;
(xv) 5HTIB ligands such as, for example, compounds disclosed in WO 99/05134 and WO 02/08212;
(xvi) mGluR2 agonists;
(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;
(xviii) chemokine receptor CCRI inhibitors; and
(xix) delta opioid agonists such as, for example, compounds disclosed in WO 97/23466 and WO 02/094794.

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples.

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Nuclear magnetic resonance (NMR) spectra were recorded at 400 MHz; the chemical shifts (δ) are reported in parts per million. Spectra were recorded using a Bruker 400 Avarice instrument fitted with a 5 mm BBFO probe or DUL probe. Instrument control was by Broker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or MeOH mixed with water containing either 0.05% formic acid or 0.025% ammonia.

Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative HPLC was performed using an Agilent Technologies 1100 Series system typically using Waters 19 mm id×100 mm long C18 columns such as XBridge or SunFire 5 μm materials at 20 mL/min. Mobile phases typically consisted of acetonitrile or MeOH mixed with water containing either 0.1% formic acid or 0.1% ammonia, unless stated otherwise.

In the following descriptions "room temperature" denotes a temperature in the range from 20° C. to 25° C.

The following abbreviations are used in the Examples:
DCM Dichloromethane
DIPEA Diisopropylethylamine
DMF Dimethyl formamide
DMSO Dimethyl sulfoxide
d6-DMSO Deuterated dimethyl sulfoxide
Et Ethyl
EtOAc Ethyl acetate
EtOH Ethanol
$Et_3N$ Triethylamine
LCMS Liquid chromatography mass spectrum
mCPBA meta-chloroperoxybenzoic acid
Me Methyl
MeOD Deuterated methanol
MeOH Methanol
MOM-Cl Methoxymethyl chloride
MS Mass spectrum
NBS N-bromosuccinimide
NMR Nuclear magnetic resonance
Ph Phenyl
PTSA para-Toluene sulfonic acid
THF Tetrahydrofuran
$Pd_2(dba)_3$ Tris(dibenzylideneacetone)dipalladium(0)
$SiO_2$ Silicon dioxide
$MgSO_4$ Magnesium sulphate
CAS Chemical Abstracts Service

1. INTERMEDIATES

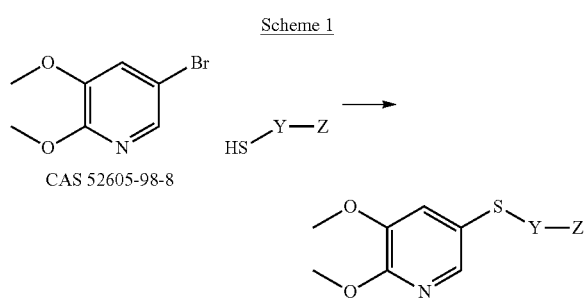

Scheme 1

CAS 52605-98-8

1.1 Intermediate 1:
5-(Benzylsulfanyl)-2,3-dimethoxypyridine

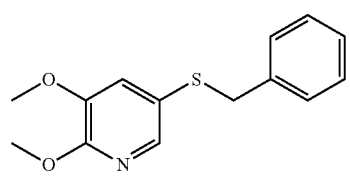 [SMILES: COc1cc(SCc2ccccc2)cnc1OC]

To a solution of 5-bromo-2,3-dimethoxypyridine (1.2 g, 5.50 mmol) in toluene (18 ml) was added phenylmethanethiol (0.71 ml, 6.05 mmol), N-ethyl-N-isopropylpropan-2-amine (2.00 ml, 12.1 mmol), $Pd_2(dba)_3$ (0.20 g, 0.22 mmol) and 4,5-bis(diphenylphosphino)-9,9-dimethylxanthene (Xantphos) (0.26 g, 0.44 mmol) at room temperature under an atmosphere of nitrogen. The reaction mixture was irradiated in the microwave with heating to 120° C. for 1 hour before being filtered through a pad of celite and washed with ethyl acetate (25 ml). The filtrate was concentrated to give an orange oil which was purified by column chromatography ($SiO_2$; 0-15% ethyl acetate in petrol) gave 5-(benzylsulfanyl)-2,3-dimethoxypyridine as an orange oil (1.52 g, 75%).

$^1$H NMR (400 MHz, $CD_2Cl_2$) δ ppm 7.70 (m, 1H) 7.18-7.37 (m, 5H) 6.86-6.92 (m, 1H) 3.94-4.04 (m, 6H) 3.72 (s, 2H). MS ES$^+$: 263.

1.2 Intermediate 2:
5-[(4-Chlorobenzyl)sulfanyl]-2,3-dimethoxypyridine

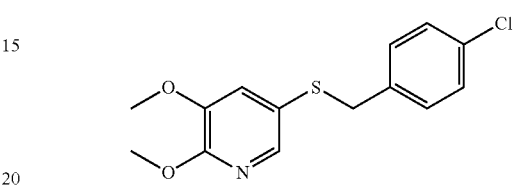

Prepared as described for 5-(benzylsulfanyl)-2,3-dimethoxypyridine (Intermediate 1) but using 4-chlorophenylmethanethiol in place of phenylmethanethiol.

$^1$H NMR (400 MHz, $CD_2Cl_2$): δ 7.69 (m, 1H), 7.29 (m, 2H), 7.16 (m, 2H), 6.92 (m, 1H), 4.01 (s, 3H), 3.98 (s, 2H), 3.76 (s, 3H).

MS ES$^+$: 296.

1.3 Intermediate 3:
2,3-Dimethoxy-5-[(4-methylbenzyl)sulfanyl]pyridine

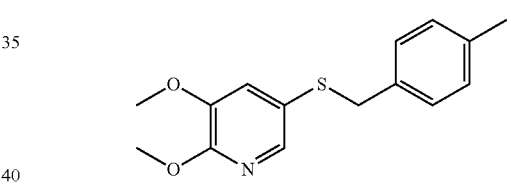

Prepared as described for 5-(benzylsulfanyl)-2,3-dimethoxypyridine (Intermediate 1) but using 4-methylphenylmethanethiol in place of phenylmethanethiol.

$^1$H NMR (400 MHz, $CD_2Cl_2$) δ 7.70 (m, 1H), 7.08-7.16 (m, 4H), 6.90 (m, 1H), 5.35 (s, 2H), 3.98 (s, 3H), 3.73 (s, 3H), 2.35 (s, 3H) MS ES$^+$: 276.

1.4 Intermediate 4:
2,3-Dimethoxy-5-[(3-methylbenzyl)sulfanyl]pyridine

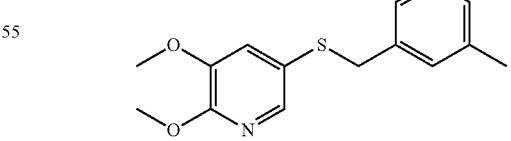

Prepared as described for 5-(benzylsulfanyl)-2,3-dimethoxypyridine (Intermediate 1) but using 3-methylphenylmethanethiol in place of phenylmethanethiol.

$^1$H NMR (400 MHz, $CD_2Cl_2$): δ 7.71 (m, 1H), 7.15-7.24 (m, 1H), 7.05-7.11 (m, 2H), 7.01 (m, 1H), 6.92 (m, 1H), 4.02 (s, 3H), 3.99 (s, 2H), 3.74 (s, 3H), 2.34 (s, 3H).

MS ES$^+$: 276.

Scheme 2.

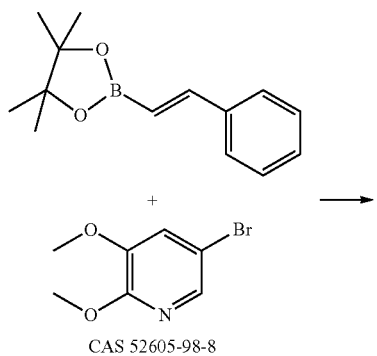

CAS 52605-98-8

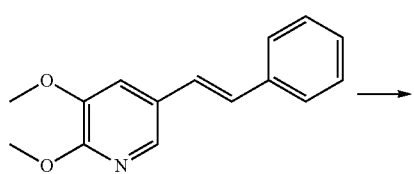

1.5. Intermediate 5:
2,3-Dimethoxy-5-[(E)-2-phenylethenyl]pyridine

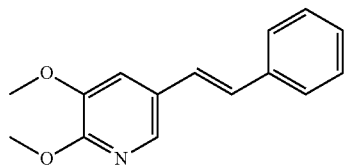 [SMILES: COc1cc(/C=C/c2ccccc2)cnc1OC]

A mixture of 5-bromo-2,3-dimethoxypyridine (0.50 g, 2.29 mmol), tripotassium phosphate (1.95 g, 9.17 mmol), tetrakistriphenylphosphine (0.27 g, 0.23 mmol) and (E)-4,4,5,5-tetramethyl-2-styryl-1,3,2-dioxaborolane (0.53 g, 2.29 mmol) was diluted with dioxane (6 ml) and water (1 ml) and heated in a microwave for 1 hour at 100° C. The reaction mixture was partitioned between ethyl acetate and water and the organics were dried (MgSO₄), filtered and concentrated in vacuo to give yellow oil. The oil was purified by column chromatography (SiO₂; 0-10% ethyl acetate in petrol) gave 2,3-dimethoxy-5-[(E)-2-phenylethenyl]pyridine as a colourless oil (116 mg, 21%).

$^1$H NMR (400 MHz, CD$_2$Cl$_2$) δ 7.82 (s, 1H), 7.56 (m, 2H), 7.41 (m, 2H), 7.26-7.36 (m, 2H), 7.02-7.16 (m, 2H), 3.98-4.06 (m, 3H), 3.94 (s, 3H)

MS ES$^+$: 242.

1.6. Intermediate 6:
2,3-Dimethoxy-5-(2-phenylethyl)pyridine

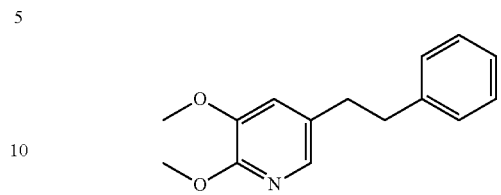

A flask containing a solution of 2,3-dimethoxy-5-[(E)-2-phenylethenyl]pyridine (Intermediate 5) (0.07 g, 0.29 mmol) in ethanol (10 ml) was evacuated and flushed with nitrogen. Palladium (10% on carbon) (0.03 g, 0.03 mmol) was added and the reaction vessel was evacuated and flushed with nitrogen before being filled with hydrogen gas from a balloon and stirred at room temperature for 45 minutes. The catalyst was removed by filtration through a pad of celite which was then washed with ethanol (20 ml). The combined organics were concentrated in vacuo to give 2,3-dimethoxy-5-(2-phenylethyl)pyridine as a colourless oil (70 mg, 99%).

$^1$H NMR (400 MHz, CD$_2$Cl$_2$): δ 7.53 (s, 1H), 7.26-7.36 (m, 2H), 7.17-7.26 (m, 3H), 6.85 (m, 1H), 3.99 (s, 3H), 3.79 (s, 3H), 2.85-2.99 (m, 4H).

MS ES$^+$: 244.

Scheme 3

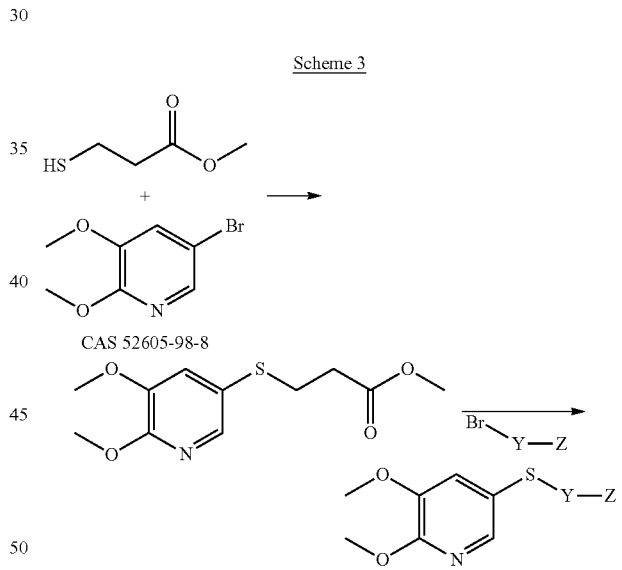

1.7. Intermediate 7: Methyl
3-[(5,6-dimethoxypyridin-3-yl)sulfanyl]propanoate

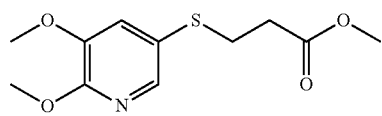

To a solution of 5-bromo-2,3-dimethoxypyridine (2 g, 9.17 mmol) in dioxane (30 ml) was added methyl 3-sulfanylpropanoate (1.21 g, 10.1 mmol), N-ethyl-N-isopropylpropan-2- amine (3.03 ml, 18.3 mmol), Pd$_2$(dba)$_3$ (0.34 g, 0.37 mmol) and Xantphos (0.43 g, 0.73 mmol) at room temperature under an atmosphere of nitrogen. The reaction was degassed by evacuating and flushing with nitrogen and heated at reflux for 18 hours and then allowed to cool and filtered, washing with ethyl acetate. The filtrate was concentrated under reduced pressure to give an orange oil. Purification by column chromatography (SiO$_2$; 0-20% ethyl acetate in petrol), gave methyl 3-[(5,6-dimethoxypyridin-3-yl)sulfanyl]propanoate as a yellow oil (2.48 g, quantitative yield).

$^1$H NMR (400 MHz, CD$_2$Cl$_2$): δ 7.81 (m, 1H), 7.20 (m, 1H), 4.01 (s, 3H), 3.88 (s, 3H), 3.69 (s, 3H), 3.08 (m, 2H), 2.61 (m, 2H).

MS ES$^+$: 258.

1.8. Intermediate 8:
5-(3-Chlorobenzylthio)-2,3-dimethoxypyridine

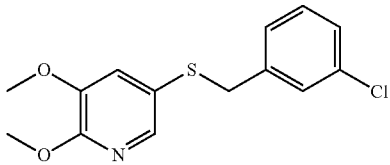 [SMILES: COc1cc(SCc2cccc(Cl)c2)cnc1OC]

To a cooled solution of methyl 3-[(5,6-dimethoxypyridin-3-yl)sulfanyl]propanoate (Intermediate 7, 257 mg, 1 mmol) in THF (6 ml) at −45° C. was added potassium tert-butoxide (123 mg, 1.10 mmol). After stirring at −45° C. for 20 minutes, 1-(bromomethyl)-3-chlorobenzene (0.16 ml, 1.20 mmol) was added and the reaction mixture was stirred with warming to room temperature for 2 hours. The resulting mixture was partitioned between ethyl acetate (15 ml) and water (15 nil) and the resulting organic layer was washed with brine (15 ml), dried (MgSO$_4$), filtered and concentrated in vacuo to give yellow oil. Purification by column chromatography (SiO$_2$; 0-10% ethyl acetate in petrol) gave 5-(3-chlorobenzylthio)-2,3-dimethoxypyridine as a yellow oil (244 mg, 82%).

$^1$H NMR (400 MHz, CD$_2$Cl$_2$): δ 7.70 (m, 1H), 7.19-7.29 (m, 3H), 7.07-7.12 (m, 1H), 6.92 (m, 1H), 3.99 (s, 2H), 3.97 (s, 2H), 3.75 (s, 3H).

MS ES$^+$: 296.

1.9. Intermediate 9:
2,3-Dimethoxy-5-[(1-phenylethyl)sulfanyl]pyridine

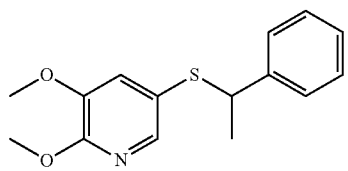 [SMILES: COc1cc(SC(C)c2ccccc2)cnc1OC]

Prepared as described for 5-(3-chlorobenzylthio)-2,3-dimethoxypyridine (Intermediate 8) but using (1-bromoethyl)benzene instead of 1-(bromomethyl)-3-chlorobenzene.

$^1$H NMR (400 MHz, CD$_2$Cl$_2$): δ7.70 (m, 1H), 7.21-7.35 (m, 5H), 6.76 (m, 1H), 4.22 (m, 1H), 3.99 (s, 3H), 3.67 (s, 3H), 1.65 (m, 3H).

MS ES$^+$: 276.

1.10. Intermediate 10:
5-[(2-Chlorobenzyl)sulfanyl]-2,3-dimethoxypyridine

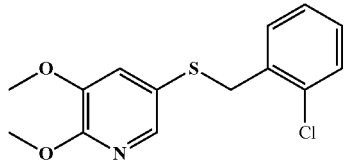

Prepared as described for 5-(3-chlorobenzylthio)-2,3-dimethoxypyridine (Intermediate 8) but using 1-(bromomethyl)-2-chlorobenzene instead of 1-(bromomethyl)-3-chlorobenzene.

$^1$H NMR (400 MHz, CD$_2$Cl$_2$): δ 7.71 (m, 1H), 7.41 (m, 1H), 7.15-7.29 (m, 2H), 7.06-7.12 (m, 1H), 6.92 (m, 1H), 4.12 (s, 2H), 3.99 (s, 3H), 3.74 (s, 3H).

MS ES$^+$: 296.

1.11. Intermediate 11: 2,3-Dimethoxy-5-{[3-(trifluoromethyl)benzyl]sulfanyl}-pyridine

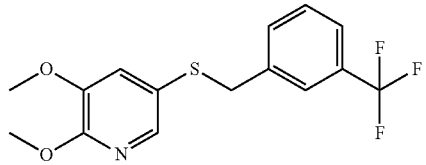 [SMILES: COc1cc(SCc2cccc(C(F)(F)F)c2)cnc1OC]

Prepared as described for 5-(3-chlorobenzylthio)-2,3-dimethoxypyridine (Intermediate 8) but using 1-(bromomethyl)-3-trifluoromethylbenzene instead of 1-(bromomethyl)-3-chlorobenzene.

$^1$H NMR (400 MHz, CD$_2$Cl$_2$): δ 7.68 (m, 1H), 7.55 (m, 1H), 7.37-7.50 (m, 3H), 6.90 (m, 1H), 4.05 (s, 2H), 3.99 (s, 3H), 3.73 (s, 3H).

MS ES$^+$: 330.

1.12. Intermediate 12:
2,3-Dimethoxy-5-[(2-methylbenzyl)sulfanyl]pyridine

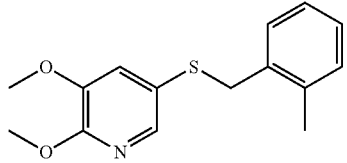 [SMILES: COc1cc(SCc2ccccc2C)cnc1OC]

Prepared as described for 5-(3-chlorobenzylthio)-2,3-dimethoxypyridine (Intermediate 8) but using 1-(bromomethyl)-2-methylbenzene instead of 1-(bromomethyl)-3-chlorobenzene.

$^1$H NMR (400 MHz, CD$_2$Cl$_2$): δ 7.73 (m, 1H), 7.15-7.26 (m, 2H), 7.09 (s, 1H), 6.97 (m, 1H), 6.84 (m, 1H), 3.95-4.08 (m, 6H), 3.72 (s, 2H), 2.39 (s, 3H).

MS ES$^+$: 276.

1.13. Intermediate 13: 5-[(3-Chloro-5-fluorobenzyl)sulfanyl]-2,3-dimethoxypyridine

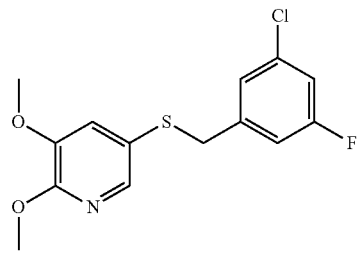 [SMILES: COc1cc(SCc2cc(F)cc(Cl)c2)cnc1OC]

Prepared as described for 5-(3-chlorobenzylthio)-2,3-dimethoxypyridine (Intermediate 8) but using 1-(bromomethyl)-3-chloro-5-fluorobenzene instead of 1-(bromomethyl)-3-chlorobenzene.

$^1$H NMR (400 MHz, DMSO-d$_6$) 7.58 (s, 1H), 7.26-7.35 (m, 1H), 7.23 (m, 1H), 7.15 (s, 1H), 7.08 (m, 1H), 4.15 (s, 2H), 3.83 (s, 3H), 3.76 (s, 3H).

MS ES$^+$: 314,

1.14. Intermediate 14: 5-(4-fluorobenzylthio)-2,3-dimethoxypyridine

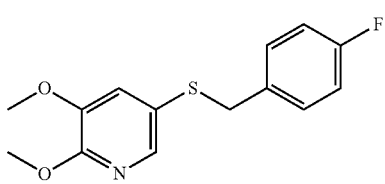 [SMILES: COc1cc(SCc2ccc(F)cc2)cnc1OC]

Prepared as described for 5-(3-chlorobenzylthio)-2,3-dimethoxypyridine (Intermediate 8) but using 1-(bromomethyl)-4-fluorobenzene instead of 1-(bromomethyl)-3-chlorobenzene.

Scheme 4.

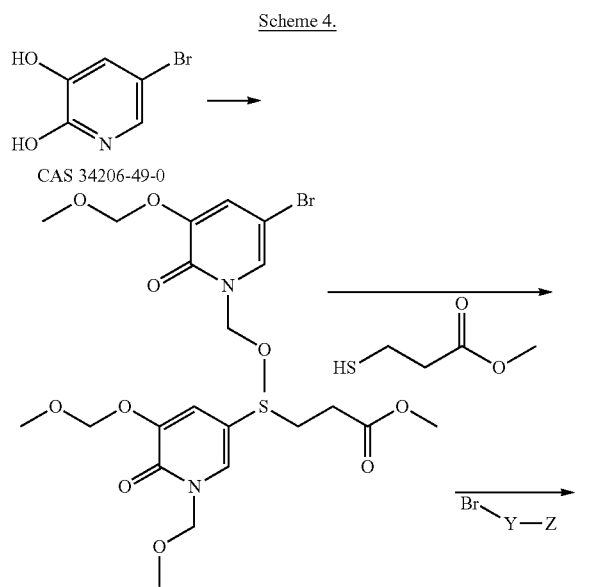

1.15. Intermediate 15: 5-Bromo-3-(methoxymethoxy)-1-(methoxymethyl)pyridin-2(1H)-one

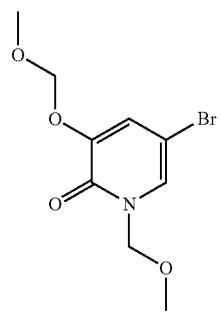

To a suspension of 5-bromopyridine-2,3-diol (5.00 g, 26.3 mmol) in DMF (100 ml) at 0° C. was added sodium hydride (1.11 g, 26.3 mmol) portion-wise. The resulting mixture was allowed to stir for 30 minutes and then methoxymethyl chloride (2.00 ml, 26.3 mmol) was added. Upon warming to room temperature and stirring for 2 hours the reaction mixture was cooled to 0° C. and a further quantity of sodium hydride (1.11 g, 26.3 mmol) was added, followed after 20 minutes by the addition of more methoxymethyl chloride (2.00 ml, 26.3 mmol). The reaction mixture was then allowed to stir at room temperature for 48 hours and then poured slowly into saturated aqueous sodium carbonate solution. The resulting mixture was extracted with ethyl acetate and the organics were evaporated and purified by column chromatography (SiO$_2$; 0-50% ethyl acetate in petrol) to yield 5-bromo-3-(methoxymethoxy)-1-(methoxymethyl)pyridin-2(1H)-one (3.8 g, 52%).

$^1$H NMR (400 MHz, DMSO-d$_6$): δ 7.66 (m, 1H), 7.10 (m, 1H), 5.22 (m, 4H), 3.39 (s, 3H), 3.28 (s, 3H).

1.16. Intermediate 16: Methyl 3-{[5-(methoxymethoxy)-1-(methoxymethyl)-6-oxo-1,6-dihydropyridin-3-yl]sulfanyl}propanoate

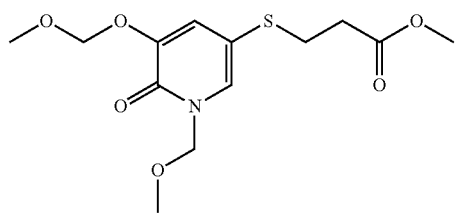

A mixture of 5-bromo-3-(methoxymethoxy)-1-(methoxymethyl)pyridin-2(1H)-one (Intermediate 15) (3.5 g, 12.6 mmol), Pd₂(dba)₃ (0.46 g, 0.50 mmol), Xantphos (0.58 g, 1.00 mmol) and DIPEA (4.40 ml, 25.2 mmol) in dioxane (60 ml) was degassed and then placed under an atmosphere of nitrogen. To this mixture was added methyl 3-mercaptopropanoate (1.66 g, 13.8 mmol) and the whole was heated under reflux for 3 hours. Upon cooling it was filtered through a pad of celite and ethyl acetate was washed through the pad of celite to recover any remaining compound. The organic filtrate was washed with water and then saturated aqueous sodium chloride solution and the organics were dried (MgSO₄), filtered and concentrated under vacuum. The crude residue was purified by column chromatography (SiO₂; 0-100% dichloromethane in petrol, then 0-10% methanol in dichloromethane). Product fractions were collected and concentrated in vacuo to give a yellow oil. This oil was purified further by reverse phase column chromatography (SiO₂—C18; 5-95% methanol in water with 0.1% formic acid) to give methyl 3-{[5-(methoxymethoxy)-1-(methoxymethyl)-6-oxo-1,6-dihydropyridin-3-yl]sulfanyl}propanoate (3.4 g, 10.7 mmol, 85%).

¹H NMR (400 MHz, DMSO-d₆): δ 7.54 (m, 1H), 7.08 (m, 1H), 5.44 (m, 2H), 5.22 (m, 2H), 3.75 (3H, s), 3.59 (s, 3H), 3.28 (s, 3H), 2.96 (m, 2H), 2.59 (m, 2H).

MS ES⁺: 318.

1.17. Intermediate 17: 5-[(4-Ethylbenzyl)sulfanyl]-3-(methoxymethoxy)-1-(methoxymethyl)pyridin-2(1H)-one

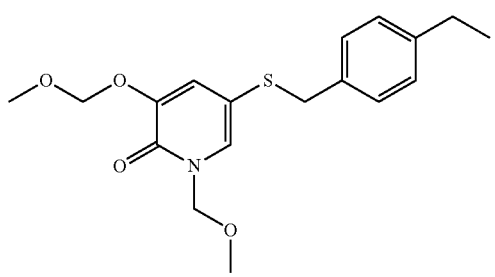 [SMILES: CCc1ccc(CSc2cc(OCOC)c(=O)n(COC)c2)cc1]

To a solution of methyl 3-{[5-(methoxymethoxy)-1-(methoxymethyl)-6-oxo-1,6-dihydropyridin-3-yl]sulfanyl}propanoate (Intermediate 16) (290 mg, 0.91 mmol) in THF (5 ml) at −45° C. was added potassium tert-butoxide (113 mg, 1.01 mmol) and the resulting mixture allowed to stir for 20 minutes. 1-(Chloromethyl)-4-ethylbenzene (170 mg, 1.10 mmol) was then added and the reaction mixture allowed to warm to room temperature and stirred for 4 hours before being quenched with water and extracted into dichlormethane. The combined organics were concentrated and subjected to column chromatography (SiO₂; 0-10% methanol in dichloromethane) to yield 5-[(4-ethylbenzyl)sulfanyl]-3-(methoxymethoxy)-1-(methoxymethyl)pyridin-2(1H)-one (253 mg, 79%).

¹H NMR (400 MHz, DMSO-d₆): δ 7.30 (m, 1H), 6.99-7.18 (m, 4H), 6.92 (m, 1H), 5.16 (s, 2H), 5.11 (s, 2H), 3.96 (s, 2H), 3.37 (s, 3H), 3.14 (s, 3H), 2.55 (m, 2H), 1.14 (m, 3H).

MS ES⁺: 350.

1.18. Intermediate 18: 3-(Methoxymethoxy)-1-(methoxymethyl)-5-({[6-(trifluoromethyl)pyridin-3-yl]methyl}sulfanyl)pyridin-2(1H)-one

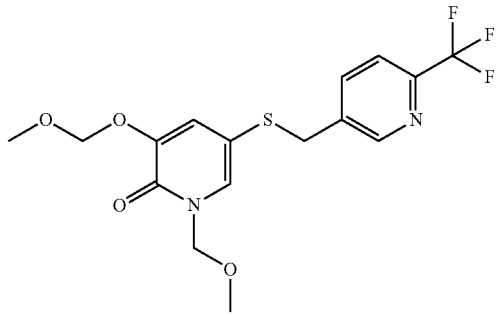 [SMILES: COCOc1cc(SCc2ccc(C(F)(F)F)nc2)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 3-(chloromethyl)-6-trifluoromethylpyridine instead of 1-(chloromethyl)-4-ethylbenzene.

¹H NMR (400 MHz, DMSO-d₆): δ 8.53 (s, 1H), 7.84 (s, 2H), 7.28 (m, 1H), 6.95, (m, 1H), 5.14 (m, 4H), 4.14 (s, 2H), 3.36 (s, 3H), 3.09 (s, 3H).

MS ES⁺: 391.

1.19. Intermediate 19: 3-(Methoxymethoxy)-1-(methoxymethyl)-5-([(3-methylpyridin-2-yl)methyl]sulfanyl)pyridin-2(1H)-one

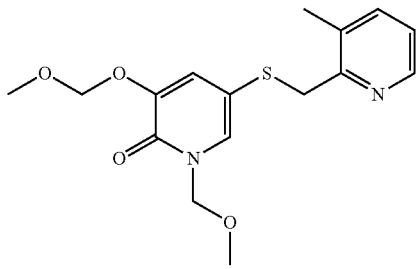 [SMILES: COCOc1cc(SCc2ncccc2C)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 2-(chloromethyl)-3-methylpyridine instead of 1-(chloromethyl)-4-ethylbenzene.

¹H NMR (400 MHz, DMSO-d₆): δ 8.25 (m, 1H), 7.57 (m, 1H), 7.38 (m, 1H), 7.17 (m, 1H), 6.87 (m, 1H), 5.18 (s, 2H), 5.10 (s, 2H), 4.12 (s, 2H), 3.36 (s, 3H), 3.20 (s, 3H), 2.31 (s, 3H).

MS ES⁺: 337.

1.20. Intermediate 20: 5-{[(3,5-Dimethyl-1,2-oxazol-4-yl)methyl]sulfanyl}-3-(methoxymethoxy)-1-(methoxymethyl)pyridin-2(1H)-one

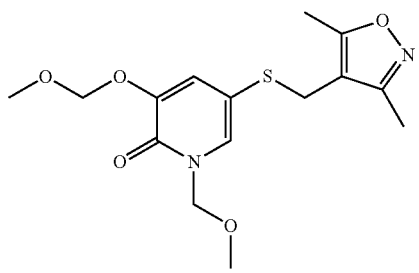 [SMILES: COCOc1cc(SCc2c(C)noc2C)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 3,5-dimethyl-4-chloromethyl-1,2-oxazole instead of 1-(chloromethyl)-4-ethylbenzene.

$^1$H NMR (400 MHz, CD$_3$OD): δ 7.35 (m, 1H), 7.01 (m, 1H), 5.31 (s, 2H), 5.19 (s, 2H), 3.77 (s, 2H), 3.48 (s, 3H), 3.33 (s, 3H), 2.24 (s, 3H) 2.11 (s, 3H).

MS ES$^+$: 341.

1.21. Intermediate 21: 3-(Methoxymethoxy)-1-(methoxymethyl)-5-{[(2-methyl-1,3-oxazol-4-yl)methyl]sulfanyl}pyridin-2(1H)-one

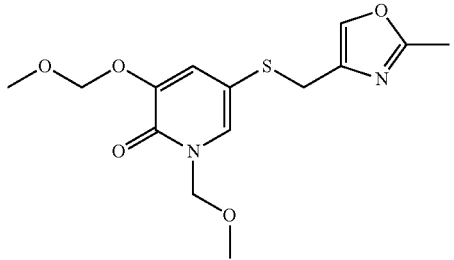

Prepared as described for 5-[(4-ethylbenzyl)sulfanyl]-3-(methoxymethoxy)-1-(methoxymethyl)pyridin-2(1H)-one (Intermediate 17) but using 2-methyl-4-chloromethyl-1,3-oxazole instead of 1-(chloromethyl)-4-ethylbenzene.

$^1$H NMR (400 MHz, CD$_3$OD): δ 7.51 (s, 1H), 7.37 (m, 1H), 7.04 (m, 1H), 5.32, (s, 2H), 5.19 (s, 2H), 3.81 (s, 2H) 3.48 (s, 3H) 3.35 (s, 3H) 2.44 (s, 3H).

MS ES$^+$: 327.

1.22. Intermediate 22: 3-(Methoxymethoxy)-1-(methoxymethyl)-5-[(pyridin-2-ylmethyl)sulfanyl]pyridin-2(1H)-one

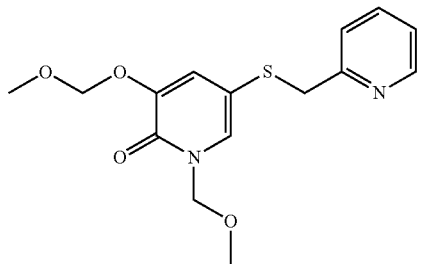 [SMILES: COCOc1cc(SCc2ccccn2)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 2-chloromethylpyridine instead of 1-(chloromethyl)-4-ethylbenzene.

$^1$H NMR (400 MHz, DMSO-d$_6$) δ 8.47 (m, 1H), 7.71 (m, 1H), 7.36 (m, 1H), 7.18-7.29 (m, 2H), 6.94 (m, 1H), 5.17 (s, 2H), 5.12 (s, 2H), 4.08 (s, 2H), 3.37 (s, 3H), 3.17 (s, 3H).

1.23. Intermediate 23: 3-(Methoxymethoxy)-1-(methoxymethyl)-5-[(pyridin-4-ylmethyl)sulfanyl]pyridin-2(1H)-one

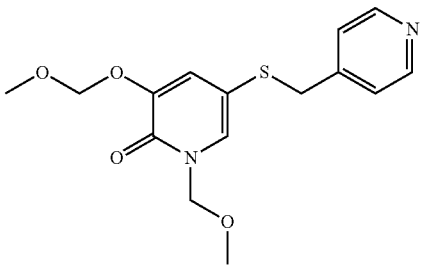 [SMILES: COCOc1cc(SCc2ccncc2)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 4-chloromethylpyridine instead of 1-(chloromethyl)-4-ethylbenzene.

$^1$H NMR (400 MHz, DMSO-d$_6$): δ 8.46 (m, 2H), 7.32 (m, 1H), 7.18 (m, 2H), 6.95 (m, 1H), 5.14 (m, 4H), 4.00 (s, 2H), 3.36 (s, 3H), 3.13 (s, 3H).

MS ES$^+$: 323.

1.24. Intermediate 24: 5-{[(5-Chloropyridin-2-yl)methyl]sulfanyl}-3-(methoxymethoxy)-1-(methoxymethyl)pyridin-2(1H)-one

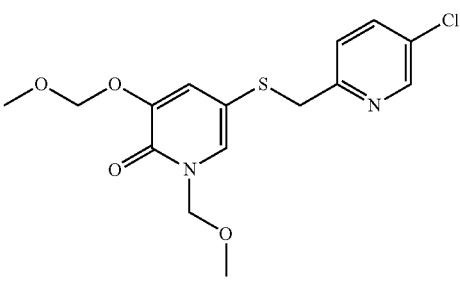 [SMILES: COCOc1cc(SCc2ccc(Cl)cn2)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 2-chloromethyl-5-chloropyridine instead of 1-(chloromethyl)-4-ethylbenzene.

MS ES$^+$: 357.

1.25. Intermediate 25: 5-[(3,4-Difluorobenzyl)sulfanyl]-3-(methoxymethoxy)-1-(methoxymethyl)pyridin-2(1H)-one

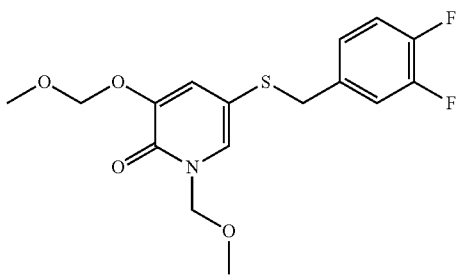 [SMILES: COCOc1cc(SCc2ccc(F)c(F)c2)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 1-(chloromethyl)-3,4-difluorobenzene instead of 1-(chloromethyl)-4-ethylbenzene.

$^1$H NMR (400 MHz, DMSO-d$_6$): δ 7.19-7.39 (m, 3H), 7.00 (m, 1H), 6.92 (m, 1H), 5.16 (m, 4H), 3.99 (s, 2H), 3.37 (s, 3H), 3.16 (s, 3H).

MS ES$^+$: 358.

1.26. Intermediate 26: 5-[(4-Methoxybenzyl)sulfanyl]-3-(methoxymethoxy)-1-(methoxymethyl)pyridin-2(1H)-one

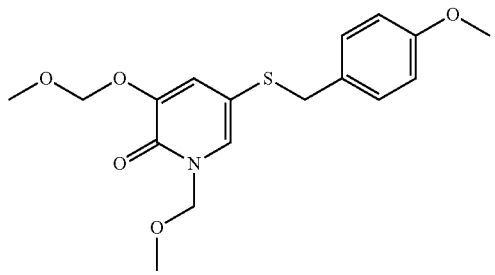

Prepared as described for 5-[(4-ethylbenzyl)sulfanyl]-3-(methoxymethoxy)-1-(methoxymethyl)pyridin-2(1H)-one (Intermediate 17) but using 1-(chloromethyl)-4-methoxybenzene instead of 1-(chloromethyl)-4-ethylbenzene.

$^1$H NMR (400 MHz, DMSO-$d_6$): δ 7.30 (m, 1H), 7.11 (m, 2H), 6.92 (m, 1H), 6.84 (m, 2H), 5.15 (m, 4H), 3.95 (s, 2H), 3.71 (s, 3H), 3.37 (s, 3H), 3.16 (s, 3H).

MS ES$^+$: 352.

1.27. Intermediate 27: 3-(Methoxymethoxy)-1-(methoxymethyl)-5-[(pyridin-3-ylmethyl)sulfanyl]pyridin-2(1H)-one

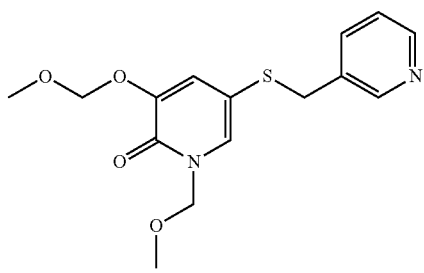 [SMILES: COCOc1cc(SCc2cccnc2)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 3-chloromethylpyridine instead of 1-(chloromethyl)-4-ethylbenzene.

$^1$H NMR (400 MHz, CD$_3$OD) δ 8.42 (br. m, 2H), 7.73 (m, 1H), 7.39 (m, 1H), 7.25 (m, 1H), 7.02 (m, 1H), 5.08-5.34 (m, 4H), 4.02 (s, 2H), 3.47 (s, 3H), 3.27 (s, 3H).

MS ES$^+$: 323.

1.28. Intermediate 28: 3-(Methoxymethoxy)-1-(methoxymethyl)-5-{[(5-methylpyridin-2-yl)methyl]sulfanyl}pyridin-2(1H)-one

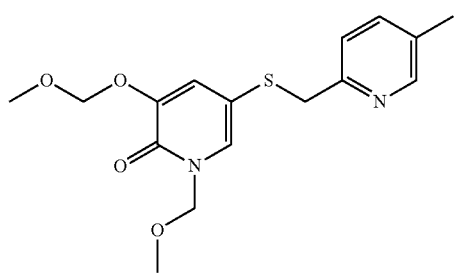

Prepared as described for 5-[(4-ethylbenzyl)sulfanyl]-3-(methoxymethoxy)-1-(methoxymethyl)pyridin-2(1H)-one (Intermediate 17) but using 2-chloromethyl-5-methylpyridine instead of 1-(chloromethyl)-4-ethylbenzene.

$^1$H NMR (400 MHz, CD$_3$OD): δ 8.29 (s, 1H), 7.47-7.72 (m, 1H), 7.12-7.35 (m, 2H), 6.97 (m, 1H), 5.02-5.36 (m, 4H), 4.03 (s, 2H) 3.46 (s, 3H) 3.29 (s, 3H) 2.34 (s, 3H).

MS ES$^+$: 337.

1.29. Intermediate 29: 3-(Methoxymethoxy)-1-(methoxymethyl)-5-[(pyrazin-2-ylmethyl)sulfanyl]pyridin-2(1H)-one

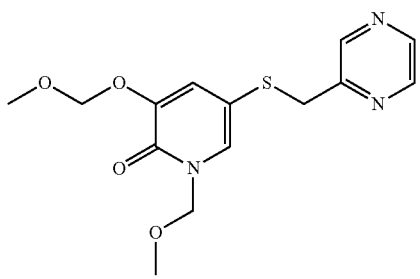 [SMILES: COCOc1cc(SCc2cnccn2)cn(COC)c1=O]

Prepared as described for 5-[(4-ethylbenzyl)sulfanyl]-3-(methoxymethoxy)-1-(methoxymethyl)pyridin-2(1H)-one (Intermediate 17) but using 2-chloromethylpyrazine instead of 1-(chloromethyl)-4-ethylbenzene.

MS ES$^+$: 324.

1.30. Intermediate 30: 3-(Methoxymethoxy)-1-(methoxymethyl)-5-{[(6-methoxypyridin-3-yl)methyl]sulfanyl}pyridin-2(1H)-one

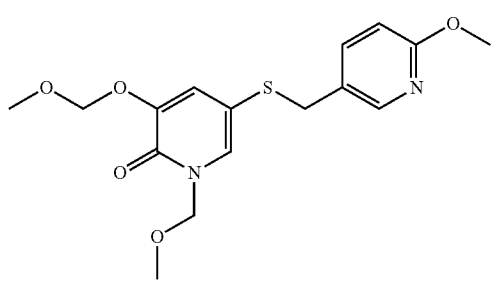

Prepared as described for 5-[(4-ethylbenzyl)sulfanyl]-3-(methoxymethoxy)-1-(methoxymethyl)pyridin-2(1H)-one (Intermediate 17) but using 3-chloromethyl-6-methoxypyridine instead of 1-(chloromethyl)-4-ethylbenzene.

$^1$H NMR (400 MHz, DMSO-$d_6$): δ 7.86 (m, 1H), 7.56 (m, 1H), 7.30 (m, 1H), 6.93 (m, 1H), 6.76 (m, 1H), 5.15 (m, 4H), 3.95 (s, 2H), 3.79 (s, 3H), 3.36 (s, 3H), 3.13 (s, 3H).

MS ES$^+$: 353.

Scheme 5

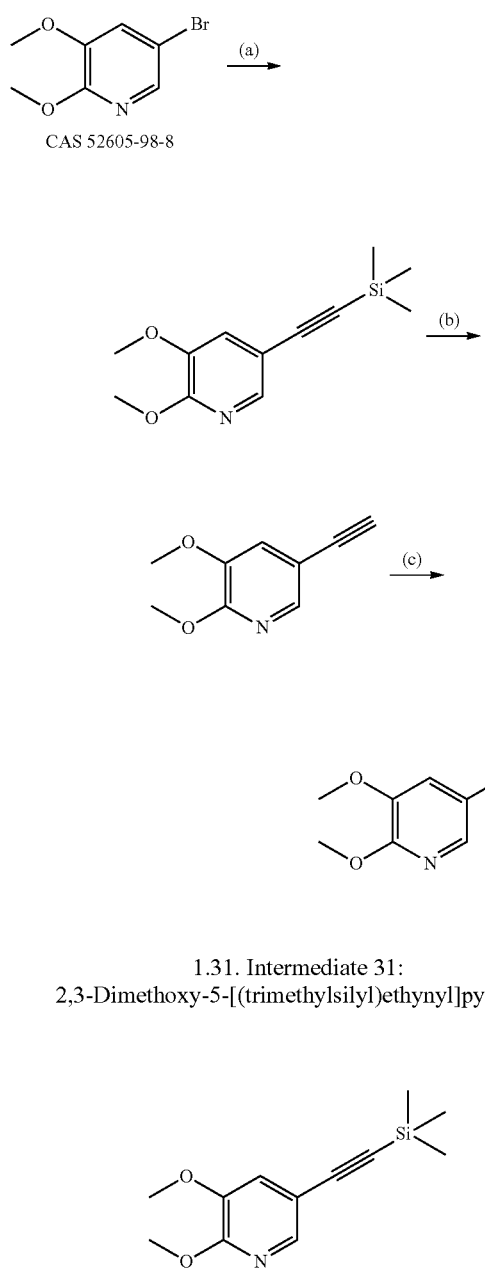

CAS 52605-98-8

1.31. Intermediate 31:
2,3-Dimethoxy-5-[(trimethylsilyl)ethynyl]pyridine

Copper (I) iodide (0.56 g, 2.9 mmol), bis(triphenylphosphine)palladium(II) dichloride (2.1 g, 2.9 mmol), and 5-bromo-2,3-dimethoxypyridine (12.8 g, 59 mmol) were added to triethylamine (80 ml) which produced a yellow suspension. The reaction was thoroughly degassed and ethynyltrimethylsilane (5.8 g, 59 mmol) was added to the stirred suspension which was then stirred for 16 hours and concentrated. The crude material was purified by column chromatography (SiO₂; 0-10% ethyl acetate in petrol) to afford 2,3-dimethoxy-5-[(trimethylsilyl)ethynyl]pyridine (9.8 g, 71%).

$^1$H NMR (400 MHz, CD$_2$Cl$_2$): δ 7.75-7.90 (m, 1H), 7.03-7.16 (m, 1H), 3.92-4.02 (m, 3H), 3.75-3.88 (m, 3H), 0.1.4-0.35 (m, 9H).

MS ES⁺: 236.

1.32. Intermediate 32:
5-Ethynyl-2,3-dimethoxypyridine 2,3-Dimethoxy-5-[(trimethylsilyl)ethynyl]pyridine (Intermediate 31) (9.8 g, 42 mmol) was dissolved in a mixture of aqueous sodium hydroxide (21 ml, 2 M, 42 mmol) and methanol (50 ml) to give a colourless solution which was stirred for 16 hours. The reaction was evaporated and the residue was partitioned between ethyl acetate and water before the organic layer was dried and concentrated in vacuo. The crude material was purified by (SiO₂; 0-10% ethyl acetate in petrol) to afford 5-ethynyl-2,3-dimethoxypyridine (5.6 g, 82%).

$^1$H NMR (400 MHz, CD$_2$Cl$_2$): δ 7.71-7.96 (m, 1H), 7.06-7.16 (m, 1H), 3.96 (s, 3H), 3.83 (s, 3H), 3.06-3.22 (m, 1H).

1.33. Intermediate 33:
2,3-Dimethoxy-5-[(2-methylphenyl)ethynyl]pyridine

Bis(triphenylphosphine)palladium(II) dichloride (50 mg, 0.07 mmol), copper (I) iodide (25 mg, 0.13 mmol) and 5-ethynyl-2,3-dimethoxypyridine (Intermediate 32) (500 mg, 3.1 mmol) were suspended in degassed triethylamine (5 ml) and dichloromethane (5 ml) to give a brown suspension. To this was added 1-iodo-2-methylbenzene (670 mg, 3.1 mmol) by syringe and the reaction was allowed to stir for 16 hours before being diluted with ethyl acetate and washed with brine. The crude material was purified by column chromatography (SiO₂; 0-10% ethyl acetate in petrol) to afford 2,3-dimethoxy-5-[(2-methylphenyl)ethynyl]pyridine (437 mg, 56% yield).

$^1$H NMR (400 MHz, CD$_2$Cl$_2$): δ 7.87-7.96 (m, 1H), 7.43-7.53 (m, 1H), 7.22-7.30 (m, 2H), 7.13-7.22 (m, 2H), 4.00 (s, 3H), 3.87 (s, 3H), 2.51 (s, 3H).

MS ES⁺: 254.

1.34. Intermediate 34: 3-Hydroxy-5-[2-(2-methylphenyl)ethyl]pyridin-2(1H)-one

Prepared as described for 2,3-dimethoxy-5-[(2-methylphenyl)ethynyl]pyridine (Intermediate 33) but using 1-iodo-3-methylbenzene instead of 1-iodo-2-methylbenzene.

$^1$H NMR (400 MHz, CD$_2$Cl$_2$) 7.89-7.92 (m, 1H), 7.30-7.38 (m, 2H), 7.21-7.28 (m, 1H), 7.14-7.20 (m, 2H), 3.99 (s, 3H), 3.86 (s, 3H), 2.36 (s, 3H).

MS ES⁺: 254.

1.35. Intermediate 35: 3-Hydroxy-5-[2-(3-methylphenyl)ethyl]pyridin-2(1H)-one

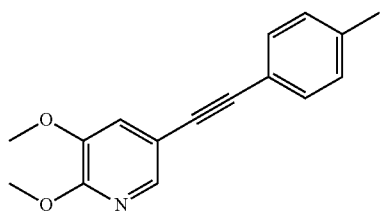

Prepared as described for 2,3-dimethoxy-5-[(2-methylphenyl)ethynyl]pyridine (Intermediate 33) but using 1-iodo-4-methylbenzene instead of 1-iodo-2-methylbenzene.

$^1$H NMR (400 MHz, CD$_2$Cl$_2$) 7.86-7.92 (m, 1H), 7.38-7.47 (m, 2H), 7.13-7.24 (m, 3H), 4.00 (s, 3H), 3.86 (s, 3H), 2.37 (s, 3H).

MS ES$^+$: 254.

1.36. Intermediate 36: 5-[(4-Fluorophenyl)ethynyl]-2,3-dimethoxypyridine

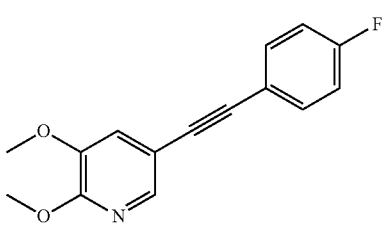 [SMILES: COc1cc(C#Cc2ccc(F)cc2)cnc1OC]

Prepared as described for 2,3-dimethoxy-5-[(2-methylphenyl)ethynyl]pyridine (Intermediate 33) but using 1-iodo-4-fluorobenzene instead of 1-iodo-2-methylbenzene.

$^1$H NMR (400 MHz, DMSO-d$_6$) 7.93 (m, 1H), 7.54-7.69 (m, 2H), 7.43 (m, 1H), 7.29 (m, 2H), 3.91 (s, 3H), 3.83 (s, 3H).

MS ES$^+$: 258.

1.37. Intermediate 37: 5-[(3-Fluorophenyl)ethynyl]-2,3-dimethoxypyridine

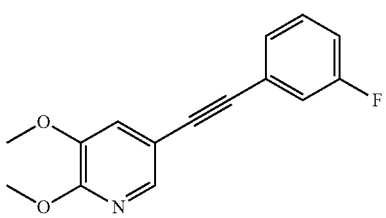 [SMILES: COc1cc(C#Cc2cccc(F)c2)cnc1OC]

Prepared as described for 2,3-dimethoxy-5-[(2-methylphenyl)ethynyl]pyridine (Intermediate 33) but using 1-iodo-3-fluorobenzene instead of 1-iodo-2-methylbenzene.

$^1$H NMR (400 MHz, DMSO-d$_6$): δ 7.95 (m, 1H), 7.35-7.55 (m, 4H), 7.29 (m, 1H), 3.91 (s, 3H), 3.84 (s, 3H).

MS ES$^+$: 258.

1.38. Intermediate 38: 5-[(2-fluorophenyl)ethynyl]-2,3-dimethoxypyridine

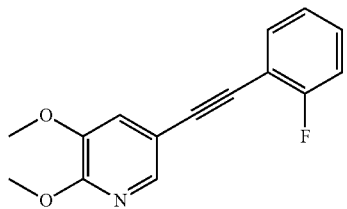 [SMILES: COc1cc(C#Cc2ccccc2F)cnc1OC]

Prepared as described for 2,3-dimethoxy-5-[(2-methylphenyl)ethynyl]pyridine (Intermediate 33) but using 1-iodo-2-fluorobenzene instead of 1-iodo-2-methylbenzene.

$^1$H NMR (400 MHz, DMSO-d$_6$): δ 7.95 (m, 1H), 7.64 (m, 1H), 7.45-7.56 (m, 1H), 7.43 (m, 1H), 7.35 (m, 1H), 7.22-7.32 (m, 1H), 3.92 (s, 3H), 3.85 (s, 3H).

MS ES$^+$: 258.

Scheme 6.

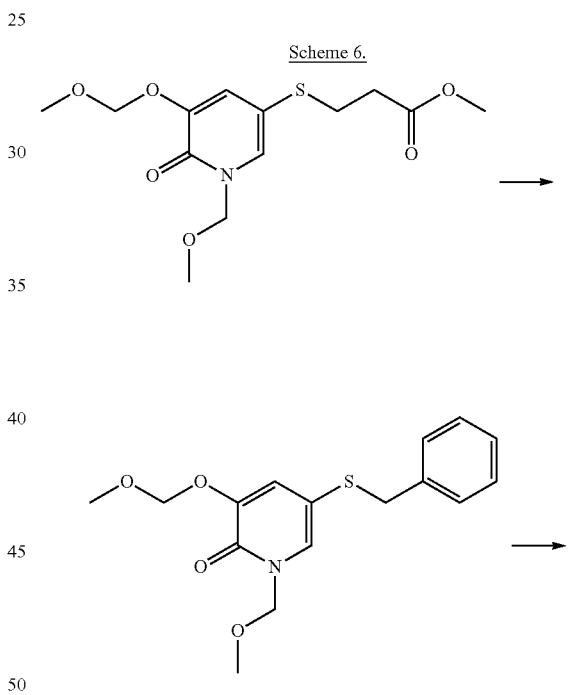

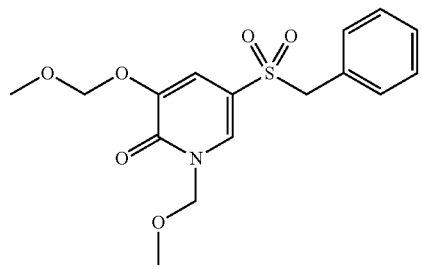

1.39. Intermediate 39: 5-(Benzylsulfanyl)-3-(methoxymethoxy)-1-(methoxymethyl)pyridin-2(1H)-one

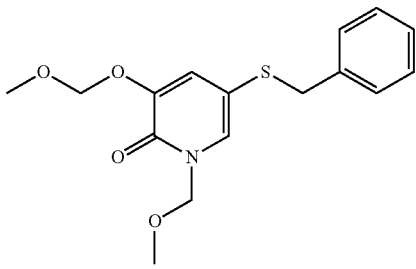 [SMILES: COCOc1cc(SCc2ccccc2)cn(COC)c1=O]

A solution of methyl 3-{[5-(methoxymethoxy)-1-(methoxymethyl)-6-oxo-1,6-dihydropyridin-3-yl]sulfanyl}propanoate (Intermediate 16; 300 mg, 0.95 mmol) in THF (5 ml) was cooled to −45° C. and potassium tert-butoxide (117 mg, 0.10 mmol) was added. After stirring at this temperature for 1 hour 1-(chloromethyl)-4-methoxybenzene (154 ml, 1134 mmol) was added and the reaction stirred for 16 hours. The reaction mixture was partitioned between dichloromethane and water. The aqueous layer was re-extracted and the combined organics dried and concentrated under reduced pressure. The resultant residue was purified by column chromatography (SiO$_2$: 80-100% ethyl acetate/petrol) to yield 5-(benzylsulfanyl)-3-(methoxymethoxy)-1-(methoxymethyl)pyridin-2(1H)-one (251 mg, 83%).

$^1$H NMR (400 MHz, DMSO-d$_6$): δ 7.15-7.36 (m, 6H), 6.88-6.98 (m, 1H), 5.16 (s, 2H), 5.12 (s, 2H), 4.00 (s, 2H), 3.36 (s, 3H), 3.15 (s, 3H).

MS ES$^+$322.

1.40. Intermediate 40: 5-(Benzylsulfonyl)-3-(methoxymethoxy)-1-(methoxy-methyl)pyridin-2(1H)-one

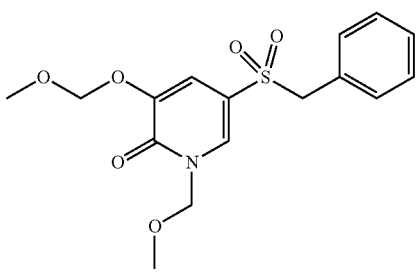 [SMILES: COCOc1cc(S(=O)(=O)Cc2ccccc2)cn(COC)c1=O]

To a suspension of 5-(benzylsulfanyl)-3-(methoxymethoxy)-1-(methoxymethyl)-pyridin-2(1H)-one (Intermediate 39; 251 mg, 0.78 mmol) in dichloromethane (5.4 ml) at 0° C. was added mCPBA (482 mg, 2.1 mmol) and the resulting mixture was allowed to warm to room temperature and stirred for 66 hours. The reaction was then quenched with water and extracted into dichloromethane and the layers were separated and the aqueous was re-extracted with further dichloromethane. The combined organics were dried and concentrated in vacuo. The resultant solid was recrystallised from dichloromethane to remove most of the benzoic acid and purified by column chromatography (SiO$_2$: 50-100% ethyl acetate/petrol and then 0-10% methanol/ethyl acetate) to yield 5-(benzylsulfonyl)-3-(methoxymethoxy)-1-(methoxymethyl)pyridin-2(1H)-one as a clear oil (75 mg, 27%).

$^1$H NMR (400 MHz, CD$_3$Cl): δ 7.48-7.52 (m, 1H), 7.31-7.39 (m, 3H), 7.20-7.26 (m, 2H), 6.86-6.97 (m, 1H), 5.27 (s, 2H), 5.14 (s, 2H), 4.36 (s, 2H), 3.48 (s, 3H), 3.30 (s, 3H).

MS ES$^+$ 354.

Scheme 7.

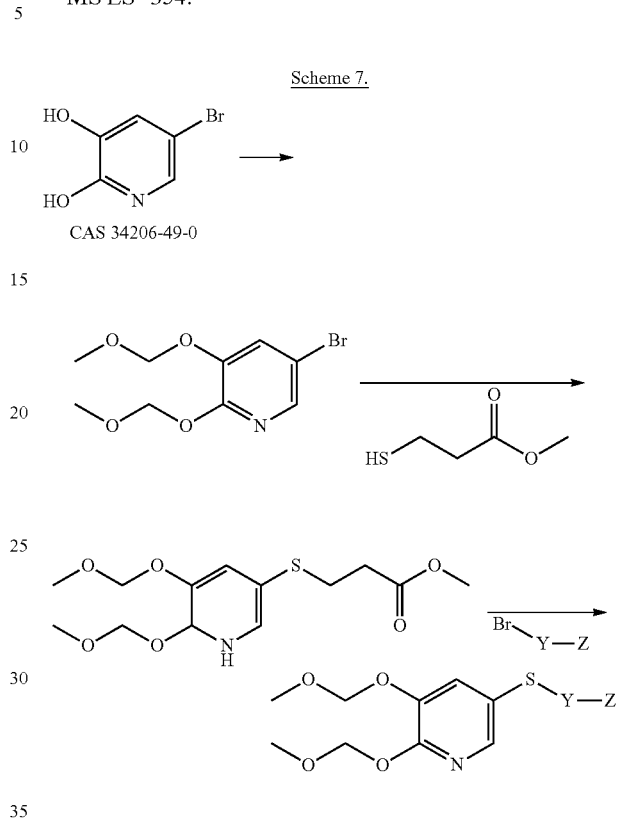

1.41. Intermediate 41: 5-Bromo-2,3-bis(methoxymethoxy)pyridine

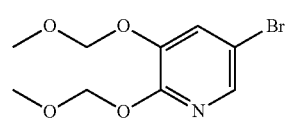

To a suspension of 5-bromopyridine-2,3-diol (9.4 g, 49.5 mmol) in DMF (165 ml) at 0° C. was added sodium hydride (1.18 g, 29.5 mmol) portion-wise and the reaction stirred for one hour at this temperature. Methoxymethyl chloride (3.8 ml, 49.5 mmol) was then added and the reaction stirred for a further 2 hours at 0° C. Sodium hydride (1.18 g, 29.5 mmol) was added and the reaction stirred for an hour at 0° C. before a further portion of methoxymethyl chloride (3.8 ml, 49.5 mmol) was added and the whole was allowed to warm and stirred for 16 hours. Upon cooling to room temperature the mixture was poured into cold saturated aqueous sodium carbonate solution. The organic materials were extracted into ethyl acetate and the layers separated before the aqueous phase, was extracted with ethyl acetate and the combined organics were then washed with brine (×7), dried (MgSO$_4$) and concentrated in vacuo. The crude product was purified by column chromatography (SiO$_2$; 0-100% ethyl acetate/petrol) to yield 5-bromo-2,3-bis(methoxymethoxy)pyridine (7.03 g, 51%).

¹H NMR (400 MHz, DMSO-d₆): δ 7.88-7.94 (m, 1H), 7.63-7.70 (m, 1H), 5.49 (s, 2H), 5.30 (s, 2H), 3.38-3.42 (m, 6H).

1.42. Intermediate 42: 3-{[5,6-bis(Methoxymethoxy)pyridin-3-yl]sulfanyl}-propanoate

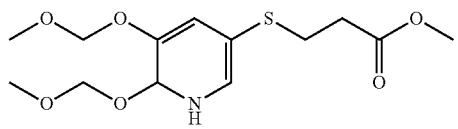

A solution of 5-bromo-2,3-bis(methoxymethoxy)pyridine (Intermediate 41; 2 g, 7.19 mmol) in dioxane 40.0 ml) was degassed and to this was added DIPEA (2.51 ml, 14.38 mmol), Xantphos (0.333 g, 0.575 mmol) and Pd₂(dba)₃ (0.263 g, 0.288 mmol). Methyl 3-mercaptopropanoate (0.951 g, 7.91 mmol) was then added as a solution in dioxane (4 mL) and the reaction was heated under reflux for 1 hour before being cooled to room temperature and filtered through a pad of celite, washing with ethyl acetate. The combined organics were washed with water and then brine, dried (MgSO₄) and then concentrated in vacuo. The crude product was purified by column chromatography (SiO₂; 0-50% ethyl acetate/petrol) to yield methyl 3-{[5,6-bis(methoxymethoxy)pyridin-3-yl]sulfanyl}propanoate (1.65 g, 72%).

¹H NMR (400 MHz, DMSO-d₆): δ 7.77-7.85 (m, 1H), 7.50-7.55 (m, 1H), 5.50 (s, 2H), 5.28 (s, 2H), 3.59 (s, 3H), 3.41 (s, 6H), 3.03-3.12 (m, 2H), 2.55-2.62 (m, 2H).

MS ES⁺ 318.

1.43. Intermediate 43: 5-[(3-Fluorobenzyl)sulfanyl]-2,3-bis(methoxymethoxy)-pyridine

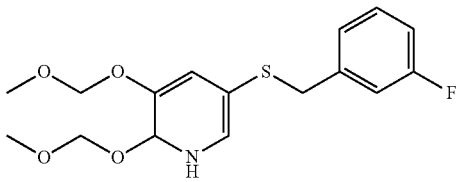 [SMILES: COCOC1=CC(SCc2cccc(F)c2)=CNC1OCOC]

To a solution of methyl 3-{[5,6-bis(methoxymethoxy)pyridin-3-yl]sulfanyl}propanoate (Intermediate 42; 1 g, 3.15 mmol) in THF (17 ml) at −45° C. was added potassium tert-butoxide (0.389 g, 3.47 mmol). After stirring at −45° C. temperature for 1 hour, 1-(bromomethyl)-3-fluorobenzene (0.715 g, 3.78 mmol) was added and the reaction mixture stirred for 3 hours. Upon warming to room temperature the reaction mixture was partitioned between dichloromethane and water. The aqueous phase was re-extracted and the combined organic extracts were washed with brine, dried and concentrated in vacuo. The crude product was purified by column chromatography (SiO₂; 0-50% ethyl acetate/petrol) to yield 5-[(3-fluorobenzyl)sulfanyl]-2,3-bis(methoxymethoxy)pyridine (690 mg, 64%).

¹H NMR (400 MHz, DMSO-d₆): δ 7.65-7.72 (m, 1H), 7.38-7.45 (m, 1H), 7.25-7.36 (m, 1H), 7.00-7.13 (m, 3H), 5.47 (s, 2H), 5.22 (s, 2H), 4.16 (s, 2H), 3.34-3.44 (m, 6H).

MS ES⁺340.

Scheme 8.

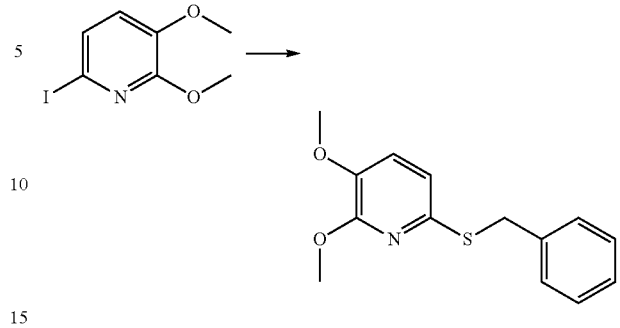

1.44. Intermediate 44: 6-(Benzylsulfanyl)-2,3-dimethoxypyridine

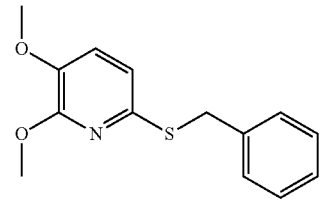 [SMILES: COc1ccc(SCc2ccccc2)nc1OC]

To a solution of 6-iodo-2,3-dimethoxypyridine (0.3 g, 1.13 mmol) in toluene (10 ml) was added phenyl mercaptan (0.21 g, 1.7 mmol) and DIPEA (0.32 g, 2.5 mmol). The reaction mass was degassed before Pd₂(dba)₃ (0.04 g, 0.05 mmol) and Xantphos (0.05 g, 0.1 mmol) were added and the whole was subjected to microwave irradiation at 120° C. with stirring for 2 hours. The resulting mixture was filtered through a pad of celite and the filtrate was added to water (60 ml) and extracted with ethyl acetate (2×30 ml). The combined organic layers were dried (Na₂SO₄) and then concentrated. The crude product was purified by column chromatography (SiO₂; 0-5% ethyl acetate/petrol) and product fractions concentrated to yield 6-(benzylsulfanyl)-2,3-dimethoxypyridine (0.2 g, 68%).

¹H NMR (400 MHz, DMSO-d₆): δ 7.40 (m, 2H), 7.29 (m, 2H), 7.22 (m, 2H), 6.85 (m, 1H), 4.35 (s, 2H), 3.89 (s, 3H), 3.72 (s, 3H).

MS ES⁺ 262.

2. EXAMPLES

Scheme A.

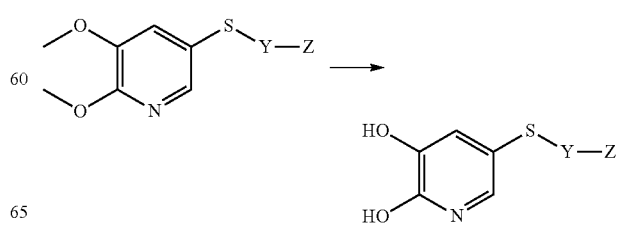

2.1. Example 1: 5-(Benzylsulfanyl)-3-hydroxypyridin-2(1H)-one

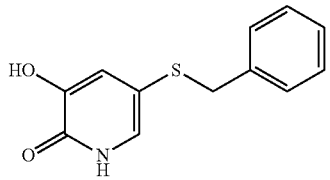

To a solution of 5-(benzylsulfanyl)-2,3-dimethoxypyridine (Intermediate 1, 1.25 g, 3.35 mmol) in THF (12 ml) was added lithium tri-sec-butylhydroborate (13.4 ml, 13.4 mmol) and the reaction was heated under reflux under an atmosphere of nitrogen for 2 hours. A further portion of lithium tri-sec-butylhydroborate (13.4 ml, 13.4 mmol) was added and the whole was heated under reflux for a further 18 hours. The reaction was quenched with water (1 ml) and evaporated onto $SiO_2$ in order to purify by column chromatography ($SiO_2$; 0-20% dichloromethane in methanol) to give a brown solid which was crystallised from ethyl acetate and ethanol to afford 5-(benzylsulfanyl)-3-hydroxypyridin-2(1H)-one as a purple solid (180 mg, 23%).

$^1$H NMR (400 MHz, DMSO-$d_6$) δ 9.10-9.15 (s, br, 1H), 7.15-7.30 (m, 5H), 6.70 (s, 2H) and 3.92 (s, 2H).
MS ES$^+$: 234.

2.2. Example 2: 5-[(4-Chlorobenzyl)sulfanyl]-3-hydroxypyridin-2(1H)-one

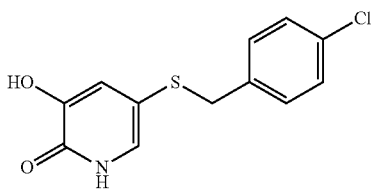 [SMILES: O=c1[nH]cc(SCc2ccc(Cl)cc2)cc1O]

Prepared as described for 5-(benzylsulfanyl)-3-hydroxypyridin-2(1H)-one (Example 1) from 5-[(4-chlorobenzyl)sulfanyl]-2,3-dimethoxypyridine (Intermediate 2).

$^1$H NMR (400 MHz, DMSO-$d_6$): δ 9.10-9.40 (s, br, 1H), 7.30-7.38 (m, 2H), 7.17-7.22 (m, 2H), 6.70 (s, 2H) and 3.94 (s, 2H).
MS ES$^+$: 268.

2.3. Example 3: 3-Hydroxy-5-[(4-methylbenzyl)sulfanyl]pyridin-2(1H)-one

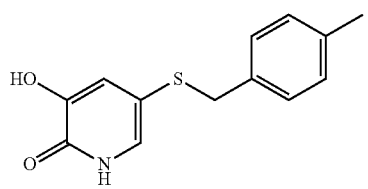 [SMILES: Cc1ccc(CSc2c[nH]c(=O)c(O)c2)cc1]

Prepared as described for 5-(benzylsulfanyl)-3-hydroxypyridin-2(1H)-one (Example 1) from 2,3-dimethoxy-5-[(4-methylbenzyl)sulfanyl]pyridine (Intermediate 3).

$^1$H NMR (400 MHz, DMSO-$d_6$): δ 9.00-9.40 (s, br, 1H), 7.10 (s, 4H), 6.70 (s, 2H), 3.90 (s, 2H) and 2.12 (s, 3H).
MS ES$^+$: 248.

2.4. Example 4: 3-Hydroxy-5-[(3-methylbenzyl)sulfanyl]pyridin-2(1H)-one

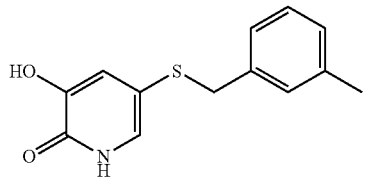 [SMILES: Cc1cccc(CSc2c[nH]c(=O)c(O)c2)c1]

Prepared as described for 5-(benzylsulfanyl)-3-hydroxypyridin-2(1H)-one (Example 1) from 2,3-dimethoxy-5-[(3-methylbenzyl)sulfanyl]pyridine (Intermediate 4).

$^1$H NMR (400 MHz, DMSO-$d_6$): δ 9.10-9.50 (s, br, 1H), 7.15-7.20 (m, 1H), 6.95-7.08 (m, 3H), 6.70 (s, 2H), 3.92 (s, 2H) and 2.16 (s, 3H).
MS ES$^+$: 248.

2.5. Example 5: 5-[(3-Chlorobenzyl)sulfanyl]-3-hydroxypyridin-2(1H)-one

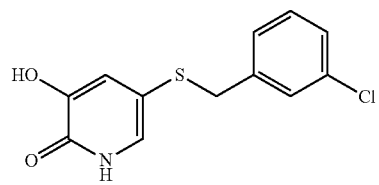 [SMILES: O=c1[nH]cc(SCc2cccc(Cl)c2)cc1O]

Prepared as described for 5-(benzylsulfanyl)-3-hydroxypyridin-2(1H)-one (Example 1) from 5-[(3-chlorobenzyl)sulfanyl]-2,3-dimethoxypyridine (Intermediate 8) except that the purification was by column chromatography. ($SiO_2$; 0-20% methanol in dichloromethane) gave a solid which was recrystallised from ethyl acetate, gave 5-[(3-chlorobenzyl)sulfanyl]-3-hydroxypyridin-2(1H)-one as a purple solid (20 mg, 9%).

$^1$H NMR (400 MHz, DMSO-$d_6$): δ 9.10-9.50 (s, br, 1H), 7.25-7.50 (m, 3H), 7.15 (s, 1H), 6.70 (s, 2H) and 3.98 (s, 2H).
MS ES$^+$: 268.

2.6. Example 6: 3-Hydroxy-5-[(1-phenylethyl)sulfanyl]pyridin-2(1H)-one

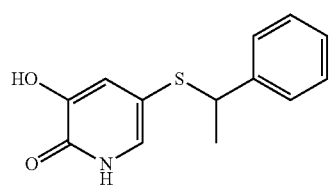 [SMILES: CC(Sc1c[nH]c(=O)c(O)c1)c1ccccc1]

Prepared as described for 5-(benzylsulfanyl)-3-hydroxypyridin-2(1H)-one (Example 1) to from 2,3-dimethoxy-5-[(1-phenylethyl)sulfanyl]pyridine (Intermediate 9).

¹H NMR (400 MHz, DMSO-d₆): δ 9.00-9.50 (s, br, 1H), 7.20-7.40 (m, 5H), 6.83 (s, 1H), 6.61 (s, 1H), 4.21-4.29 (m, 1H) and 1.51 (s, 3H).

MS ES⁺: 248.

2.7. Example 7: 5-[(2-Chlorobenzyl)sulfanyl]-3-hydroxypyridin-2(1H)-one

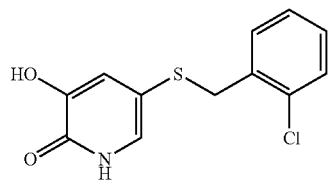

Prepared as described for 5-(benzylsulfanyl)-3-hydroxypyridin-2(1H)-one (Example 1) from 5-[(2-chlorobenzyl)sulfanyl]-2,3-dimethoxypyridine (Intermediate 10).

¹H NMR (400 MHz, DMSO-d₆): δ 9.10-9.40 (s, br, 1H), 7.42-7.45 (m, 1H), 7.25-7.30 (m, 2H), 7.15-7.20 (m, 1H), 6.71 (s, 2H) and 4.01 (s, 2H).

MS ES⁺: 268.

2.8. Example 8: 3-Hydroxy-5-{[3-(trifluoromethyl)benzyl]sulfanyl}pyridin-2(1H)-one

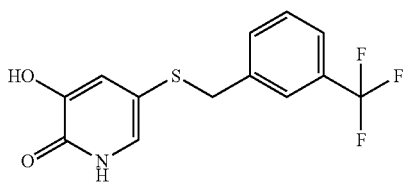 [SMILES: O=c1[nH]cc(SCc2cccc(C(F)(F)F)c2)cc1O]

Prepared as described for 5-(benzylsulfanyl)-3-hydroxypyridin-2(1H)-one (Example 1) from 2,3-dimethoxy-5-{[3-(trifluoromethyl)benzyl]sulfanyl}pyridine (Intermediate 11).

¹H NMR (400 MHz, DMSO-d₆): δ 9.10-9.40 (s, br, 1H), 7.45-7.65 (m, 4H), 6.69 (s, 2H) and 4.18 (s, 2H).

MS ES⁺: 302.

2.9. Example 9: 3-Hydroxy-5-[(2-methylbenzyl)sulfanyl]pyridin-2(1H)-one

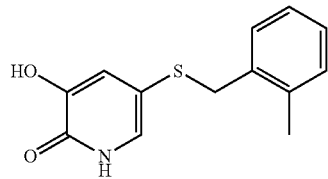 [SMILES: Cc1ccccc1CSc1c[nH]c(=O)c(O)c1]

Prepared as described for 5-(benzylsulfanyl)-3-hydroxypyridin-2(1H)-one (Example 1) from 2,3-dimethoxy-5-[(2-methylbenzyl)sulfanyl]pyridine (Intermediate 12).

¹H NMR (400 MHz, DMSO-d₆): δ 9.00-9.70 (s, br, 1H), 7.13-7.18 (m, 2H), 7.05-7.11 (m, 1H), 6.96-7.02 (m, 1H), 6.73 (s, 2H), 3.98 (s, 2H) and 2.31 (s, 3H).

MS ES⁺: 248.

2.10. Example 10: 5-[(3-Chloro-5-fluorobenzyl)sulfanyl]-3-hydroxypyridin-2(1H)-one

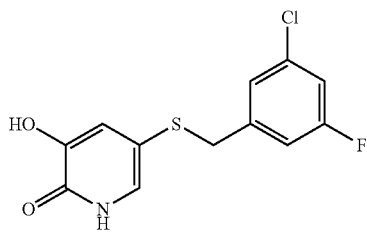 [SMILES: O=c1[nH]cc(SCc2cc(F)cc(Cl)c2)cc1O]

Prepared as described for 5-(benzylsulfanyl)-3-hydroxypyridin-2(1H)-one (Example 1) from 5-[(3-chloro-5-fluorobenzyl)sulfanyl]-2,3-dimethoxypyridine (Intermediate 13).

¹H NMR (400 MHz, CD₃OD): δ 7.01-7.10 (m, 2H), 6.90-6.94 (m, 1H), 6.82-6.88 (m, 2H) and 3.90 (s, 2H).

MS ES⁺: 286.

2.11. Example 11: 5-[(4-Fluorobenzyl)sulfanyl]-3-hydroxypyridin-2(1H)-one

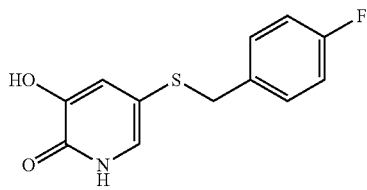 [SMILES: O=c1[nH]cc(SCc2ccc(F)cc2)cc1O]

Prepared as described for 5-(benzylsulfanyl)-3-hydroxypyridin-2(1H)-one (Example 1) from 5-(4-fluorobenzylthio)-2,3-dimethoxypyridine (Intermediate 14).

¹H NMR (400 MHz, DMSO-d₆): δ 9.18-9.35 (s, br, 1H), 7.18-7.25 (m, 2H), 7.08-7.16 (m, 2H), 6.70 (s, 2H) and 3.95 (s, 2H).

MS ES⁺: 252.

2.12. Example 12: 5-[(4-Ethylbenzyl)sulfanyl]-3-hydroxypyridin-2(1H)-one

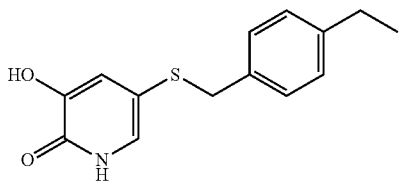 [SMILES: CCc1ccc(CSc2c[nH]c(=O)c(O)c2)cc1]

A solution of 5-[(4-ethylbenzyl)sulfanyl]-3-(methoxymethoxy)-1-(methoxymethyl)-pyridin-2(1H)-one (253 mg, 0.724 mmol) (Intermediate 17) in hydrogen chloride solution (4 M in dioxane; 2.10 ml, 8.50 mmol) and dioxane (2 ml) was heated under reflux overnight. The reaction mixture was concentrated in vacuo and the resulting solid was recrystallised in boiling ethanol/water. The resulting recrystallised solid was filtered and dried to yield 5-[(4-ethylbenzyl)sulfanyl]-3-hydroxypyridin-2(1H)-one (45 mg, 0.17 mmol, 20% yield).

$^1$H NMR (400 MHz, DMSO-$d_6$): δ 9.10-9.40 (s, br, 1H), 7.13 (s, 4H), 6.73 (m, 2H), 3.93 (s, 2H), 2.50-2.60 (m, 2H, partially obscured by solvent signal) and 1.15-1.22 (m, 3H).

MS ES$^+$: 262.

2.13. Example 13: 3-Hydroxy-5-({[6-(trifluoromethyl)pyridin-3-yl]methyl}-sulfanyl)pyridin-2(1H)-one

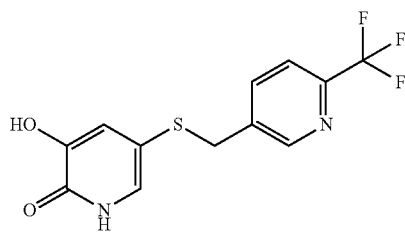 [SMILES: O=c1[nH]cc(SCc2ccc(C(F)(F)F)nc2)cc1O]

Prepared as described for 5-(benzylsulfanyl)-3-hydroxypyridin-2(1H)-one (Example 12) from 3-(methoxymethoxy)-1-(methoxymethyl)-5-({[6-(trifluoromethyl)pyridin-3-yl]methyl}sulfanyl)pyridin-2(1H)-one (Intermediate 18).

$^1$H NMR (400 MHz, DMSO-$d_6$): δ 9.10-9.60 (s, br, 1H), 8.55 (s, 1H), 7.85 (s, 2H), 6.68 (s, 2H) and 4.04 (s, 2H).

MS ES$^+$: 303.

2.14. Example 14: 3-Hydroxy-5-{[(3-methylpyridin-2-yl)methyl]sulfanyl}pyridin-2(1H)-one

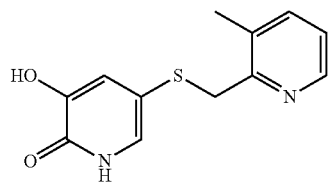 [SMILES: Cc1cccnc1CSc1c[nH]c(=O)c(O)c1]

Prepared as described for 5-(benzylsulfanyl)-3-hydroxypyridin-2(1H)-one (Example 12) from 3-(methoxymethoxy)-1-(methoxymethyl)-5-{[(3-methylpyridin-2-yl)methyl]sulfanyl}pyridin-2(1H)-one (Intermediate 19).

$^1$H NMR (400 MHz, DMSO-$d_6$): δ 8.90-9.60 (s, br, 1H), 8.53 (s, 1H), 8.18 (s, 1H), 7.68 (s, 1H), 6.82 (s, 1H), 6.58 (s, 2H), 4.23 (s, 2H) and 2.41 (s, 3H).

MS ES$^+$: 249.

2.15. Example 15: 5-{[(3,5-Dimethyl-1,2-oxazol-4-yl)methyl]sulfanyl}-3-hydroxypyridin-2(1H)-one

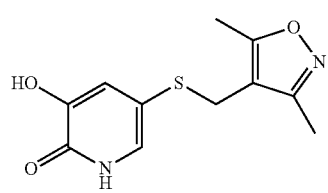 [SMILES: Cc1noc(C)c1CSc1c[nH]c(=O)c(O)c1]

Prepared as described for 5-(benzylsulfanyl)-3-hydroxypyridin-2(1H)-one (Example 12) from 5-{[(3,5-dimethyl-1,2-oxazol-4-yl)methyl]sulfanyl}-3-(methoxymethoxy)-1-(methoxymethyl)pyridin-2(1H)-one (Intermediate 20).

$^1$H NMR (400 MHz, DMSO-$d_6$): δ 9.26 (s, 1H), 6.78 (s, 1H), 6.72 (s, 1H), 3.76 (s, 2H), 2.15 (s, 3H) and 2.10 (s, 3H).

MS ES$^+$: 253.

2.16. Example 16: 3-Hydroxy-5-{[(2-methyl-1,3-oxazol-4-yl)methyl]sulfanyl}-pyridin-2(1H)-one

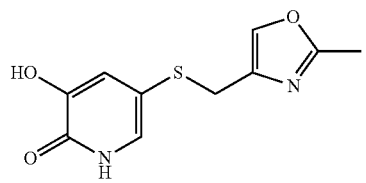 [SMILES: Cc1nc(CSc2c[nH]c(=O)c(O)c2)co1]

Prepared as described for 5-(benzylsulfanyl)-3-hydroxypyridin-2(1H)-one (Example 12) from 3-(methoxymethoxy)-1-(methoxymethyl)-5-{[(2-methyl-1,3-oxazol-4-yl)methyl]sulfanyl}pyridin-2(1H)-one (Intermediate 21).

$^1$H NMR (400 MHz, CD$_3$OD) δ 7.47 (s, 1H), 6.70-6.95 (m, 2H), 3.82 (s, 2H) and 2.54 (s, 3H).

MS ES$^+$: 239.

2.17. Example 17: 3-Hydroxy-5-[(pyridin-2-ylmethyl)sulfanyl]pyridin-2(1H)-one

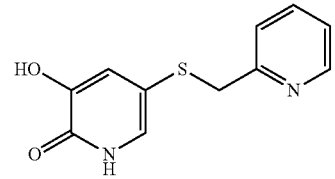 [SMILES: O=c1[nH]cc(SCc2ccccn2)cc1O]

Prepared as described for 5-(benzylsulfanyl)-3-hydroxypyridin-2(1H)-one (Example 12) from 3-(methoxymethoxy)-1-(methoxymethyl)-5-[(pyridin-2-ylmethyl)sulfanyl]pyridin-2(1H)-one (Intermediate 22).

$^1$H NMR (400 MHz, CD$_3$OD) δ 8.65 (s, 1H), 8.18 (s, 1H), 7.65-7.70 (m, 1H), 7.57-7.63 (m, 2H), 6.90 (s, 1H), 6.80 (s, 1H) and 4.18 (s, 2H).

MS ES$^+$: 235.

2.18. Example 18: 3-Hydroxy-5-[(pyridin-4-ylmethyl)sulfanyl]pyridin-2(1H)-one

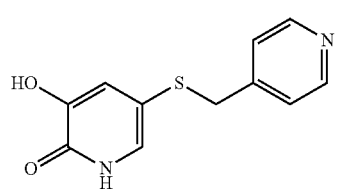 [SMILES: O=c1[nH]cc(SCc2ccncc2)cc1O]

Prepared as described for 5-(benzylsulfanyl)-3-hydroxypyridin-2(1H)-one (Example 12) from 3-(methoxymethoxy)-1-(methoxymethyl)-5-[(pyridin-4-ylmethyl)sulfanyl]pyridin-2(1H)-one (Intermediate 23).
¹H NMR (400 MHz, CD₃OD) δ 8.45 (s, 2H), 7.27 (s, 2H), 6.81 (s, 1H), 6.75 (s, 1H) and 3.99 (s, 2H).
MS ES⁺: 235.

2.19. Example 19: 5-{[(5-Chloropyridin-2-yl)methyl]sulfanyl}-3-hydroxypyridin-2(1H)-one

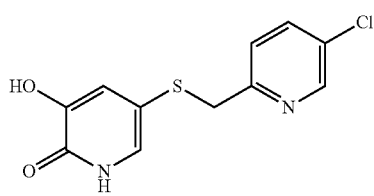 [SMILES: O=c1[nH]cc(SCc2ccc(Cl)cn2)cc1O]

Prepared as described for 5-(benzylsulfanyl)-3-hydroxypyridin-2(1H)-one (Example 12) from 5-{[(5-chloropyridin-2-yl)methyl]sulfanyl}-3-(methoxymethoxy)-1-(methoxymethyl)pyridin-2(1H)-one (Intermediate 24).
¹H NMR (400 MHz, CD₃OD) δ 8.45 (s, 1H), 7.78 (s, 1H), 727 (s, 1H), 6.81 (s, 2H), 6.75 (s, 1H) and 3.99 (s, 2H).
MS ES⁺: 269.

2.20. Example 20: 5-[(3,4-Difluorobenzyl)sulfanyl]-3-hydroxypyridin-2(1H)-one

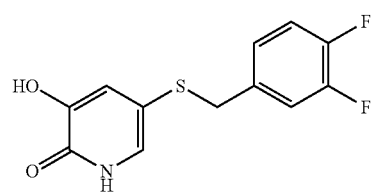 [SMILES: O=c1[nH]cc(SCc2ccc(F)c(F)c2)cc1O]

Prepared as described for 5-(benzylsulfanyl)-3-hydroxypyridin-2(1H)-one (Example 12) from 5-[(3,4-difluorobenzyl)sulfanyl]-3-(methoxymethoxy)-1-(methoxymethyl)pyridin-2(1H)-one (Intermediate 25).
¹H NMR (400 MHz, DMSO-d₆): δ 9.27 (s, 1H), 7.23-7.38 (m, 2H), 6.95-7.04 (m, 1H), 6.67-6.73 (m, 2H) and 3.95 (s, 2H).
MS ES⁺: 270.

2.21. Example 21: 3-Hydroxy-5-[(4-methoxybenzyl)sulfanyl]pyridin-2(1H)-one

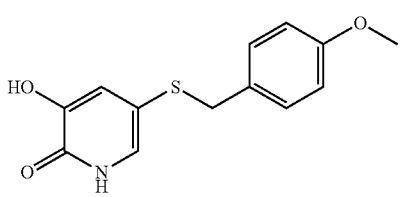 [SMILES: COc1ccc(CSc2c[nH]c(=O)c(O)c2)cc1]

Prepared as described for 5-(benzylsulfanyl)-3-hydroxypyridin-2(1H)-one (Example 12) from 5-[(4-methoxybenzyl)sulfanyl]-3-(methoxymethoxy)-1-(methoxymethyl)pyridin-2(1H)-one (Intermediate 26).

¹H NMR (400 MHz, DMSO-d₆): δ 9.00-9.40 (s, br, 1H), 7.08-7.13 (m, 2H), 6.83-6.94 (m, 2H), 6.67-6.75 (m, 2H), 3.90 (s, 2H) and 3.83 (s, 3H).
MS ES⁺: 264.

2.22. Example 22: 3-Hydroxy-5-[(pyridin-3-ylmethyl)sulfanyl]pyridin-2(1H)-one

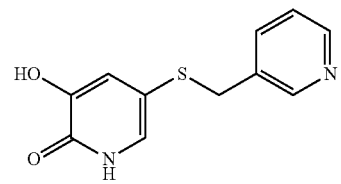 [SMILES: O=c1[nH]cc(SCc2cccnc2)cc1O]

Prepared as described for 5-(benzylsulfanyl)-3-hydroxypyridin-2(1H)-one (Example 12) from 3-(methoxymethoxy)-1-(methoxymethyl)-5-[(pyridin-3-ylmethyl)sulfanyl]pyridin-2(1H)-one (Intermediate 27).
¹H NMR (400 MHz, DMSO-d₆): δ 9.00-9.80 (s, br, 1H), 8.70-8.75 (m, 1H), 8.58-8.64 (m, 1H), 8.23-8.28 (m, 1H), 7.76-7.85 (m, 1H), 7.66 (s, 1H), 7.76 (s, 1H) and 4.15 (s, 2H).
MS ES⁺: 235.

2.23. Example 23: 3-Hydroxy-5-{[(5-methylpyridin-2-yl)methyl]sulfanyl}pyridin-2(1H)-one

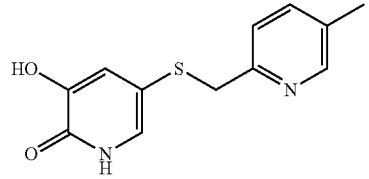 [SMILES: Cc1ccc(CSc2c[nH]c(=O)c(O)c2)nc1]

Prepared as described for 5-(benzylsulfanyl)-3-hydroxypyridin-2(1H)-one (Example 12) from 3-(methoxymethoxy)-1-(methoxymethyl)-5-{[(5-methylpyridin-2-yl)methyl]sulfanyl}pyridin-2(1H)-one (Intermediate 28).
¹H NMR (400 MHz, DMSO-d₆): δ 9.00-9.40 (s, br, 1H), 8.63 (s, 1H), 8.15-8.20 (m, 1H), 7.56-7.66 (m, 1H), 6.78 (s, 1H), 6.66 (s, 1H), 4.22 (s, 2H) and 2.38 (s, 3H).
MS ES⁺: 249.

2.24. Example 24: 3-Hydroxy-5-[(pyrazin-2-ylmethyl)sulfanyl]pyridin-2(1H)-one

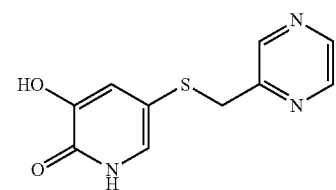 [SMILES: O=c1[nH]cc(SCc2cnccn2)cc1O]

Prepared as described for 5-(benzylsulfanyl)-3-hydroxypyridin-2(1H)-one (Example 12) from 3-(methoxymethoxy)-1-(methoxymethyl)-5-[(pyrazin-2-ylmethyl)sulfanyl]pyridin-2(1H)-one (Intermediate 29).

¹H NMR (400 MHz, DMSO-d₆): δ 9.10-9.60 (s, 1H), 8.46-8.58 (m, 3H), 6.74-6.78 (m, 1H), 6.67 (s, 1H) and 4.02 (s, 2H).
MS ES⁺: 236.

2.25. Example 25: 3-Hydroxy-5-{[(6-methoxypyridin-3-yl)methyl]-sulfanyl}-pyridin-2(1H)-one

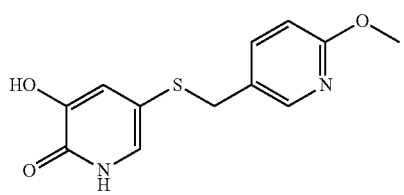 [SMILES: COc1ccc(CSc2c[nH]c(=O)c(O)c2)cn1]

Prepared as described for 5-(benzylsulfanyl)-3-hydroxypyridin-2(1H)-one (Example 12) from 3-(methoxymethoxy)-1-(methoxymethyl)-5-{[(6-methoxypyridin-3-yl)methyl]sulfanyl}pyridin-2(1H)-one (Intermediate 30).

¹H NMR (400 MHz, DMSO-d₆): δ 9.00-9.60 (s, 1H), 7.85-7.89 (m, 1H), 7.53-7.58 (m, 1H), 6.78-6.83 (s, 1H), 6.71 (s, 2H), 3.91 (s, 2H) and 3.80 (s, 2H).
MS ES⁺: 265.

Scheme B

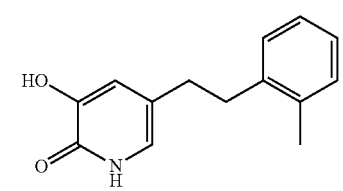 [SMILES: Cc1ccccc1CCc1c[nH]c(=O)c(O)c1]

2.26. Example 26: 3-Hydroxy-5-(2-methylphenethyl)pyridin-2(1H)-one 2,3-Dimethoxy-5-[(2-methylphenyl)ethynyl]pyridine (Intermediate 33) (437 mg, 1.7 mmol) was hydrogenated in methanol using palladium on carbon as catalyst at 20 bar. The crude product was dissolved in acetic acid (5 ml) and 48% aqueous hydrobromic acid (5 ml) was added before the mixture was irradiated in the microwave with heating at 180° C. for 1 hour. The resulting mixture was then poured into water and the precipitated solid was filtered off and washed with water before being recrystallised from ethanol (twice) to afford 3-hydroxy-5-(2-methylphenethyl)pyridin-2(1H)-one (70 mg, 0.3 mmol, 18% yield).

¹H NMR (400 MHz, DMSO-d₆): δ 8.84-8.90 (s, br, 1H), 7.05-7.18 (m, 4H), 6.71 (s, 1H), 6.62 (s, 1H), 2.75-2.80 (m, 2H), 2.50-2.60 (m, 2H, partially obscured by solvent signal) and 2.28 (s, 3H).
MS ES⁺: 230.

2.27. Example 27: 3-Hydroxy-5-(2-phenylethyl)pyridin-2(1H)-one

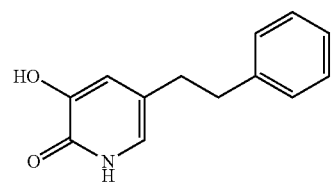 [SMILES: O=c1[nH]cc(CCc2ccccc2)cc1O]

Prepared as described for 3-Hydroxy-5-(2-methylphenethyl)pyridin-2(1H)-one (Example 26) from 2,3-dimethoxy-5-(2-phenylethyl)pyridine (Intermediate 6). Purification by column chromatography (C18-SiO₂; 5-95% methanol in water with 0.01% formic acid) gave 3-hydroxy-5-(2-phenylethyl)pyridin-2(1H)-one as a purple solid (10 mg, 16%).

¹H NMR (400 MHz, DMSO-d₆): δ 8.90-9.80 (s, br, 1H), 7.30-7.40 (m, 3H), 7.17-7.25 (m, 2H), 6.68 (s, 2H) and 3.90 (s, 2H).
MS ES⁺: 216.

2.28. Example 28: 3-Hydroxy-5-[2-(3-methylphenyl)ethyl]pyridin-2(1H)-one

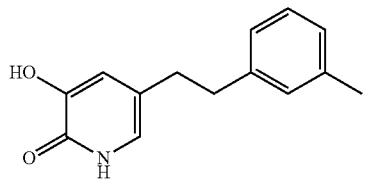 [SMILES: Cc1cccc(CCc2c[nH]c(=O)c(O)c2)c1]

Prepared as described for 3-hydroxy-5-(2-methylphenethyl)pyridin-2(1H)-one (Example 27) from 2,3-dimethoxy-5-[(3-methyl-phenyl)ethynyl]pyridine (Intermediate 34).

¹H NMR (400 MHz, DMSO-d₆): δ 8.84 (s, 1H), 7.08 (s, 4H), 6.68-6.69 (m, 1H), 6.58-6.61 (m, 1H), 2.73-2.80 (m, 2H), 2.55-2.60 (m, 2H, partially obscured by solvent signal) and 2.28 (s, 3H).
MS ES⁺: 230.

2.29. Example 29: 3-Hydroxy-5-[2-(4-methylphenyl)ethyl]pyridin-2(1H)-one

Prepared as described for 3-hydroxy-5-(2-methylphenethyl)pyridin-2(1H)-one (Example 27) from 2,3-dimethoxy-5-[(4-methylphenyl)ethynyl]pyridine (Intermediate 35).

¹H NMR (400 MHz, DMSO-d₆): δ 11.37 (br. s, 1H), 8.82 (s, 1H), 7.06 (s, 4H), 6.63-6.71 (m, 1H), 6.56 (s, 1H), 2.66-2.76 (m, 2H), 2.47-2.62 (m, 2H), 2.25 (s, 3H).
MS ES⁺: 230.

2.30. Example 30: 5-[2-(4-Fluorophenyl)ethyl]-3-hydroxypyridin-2(1H)-one

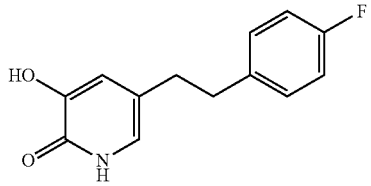 [SMILES: O=c1[nH]cc(CCc2ccc(F)cc2)cc1O]

Prepared as described for 3-hydroxy-5-(2-methylphenethyl)pyridin-2(1H)-one (Example 27) from 5-[(4-fluorophenyl)ethynyl]-2,3-dimethoxypyridine (Intermediate 36).

¹H NMR (400 MHz, DMSO-d₆): δ 8.75-9.00 (s, br, 1H), 7.22-7.28 (m, 2H), 7.02-7.12 (m, 2H), 6.70 (m, 1H), 6.61 (m, 1H), 2.75-2.83 (m, 2H) and 2.50-2.60 (m, 2H, partially obscured by solvent signal).
MS ES⁺: 234.

2.31. Example 31: 5-[2-(3-Fluorophenyl)ethyl]-3-hydroxypyridin-2(1H)-one

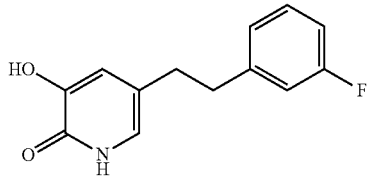 [SMILES: O=c1[nH]cc(CCc2cccc(F)c2)cc1O]

Prepared as described for 3-hydroxy-5-(2-methylphenethyl)pyridin-2(1H)-one (Example 27) from 5-[(3-fluorophenyl)ethynyl]-2,3-dimethoxypyridine (Intermediate 37).

¹H NMR (400 MHz, DMSO-d₆): δ 8.75-8.95 (s, br, 1H), 7.28-7.38 (m, 1H), 6.95-7.15 (m, 3H), 6.70 (m, 1H), 6.61 (m, 1H), 2.78-2.85 (m, 2H) and 2.57-2.68 (m, 2H).
MS ES⁺: 234.

2.32. Example 32: 5-[2-(2-Fluorophenyl)ethyl]-3-hydroxypyridin-2(1H)-one

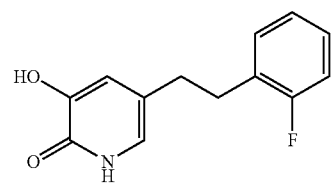

Prepared as described for 3-hydroxy-5-(2-methylphenethyl)pyridin-2(1H)-one (Example 27) from 5-[(2-fluorophenyl)ethynyl]-2,3-dimethoxypyridine (Intermediate 38).

¹H NMR (400 MHz, DMSO-d₆): δ 8.88 (s, 1H), 7.21-7.31 (m, 2H), 7.08-715 (m, 2H), 6.68 (m, 1H), 6.57 (m, 1H), 2.78-2.88 (m, 2H) and 2.55-2.62 (m, 2H).
MS ES⁺: 234.

Scheme C

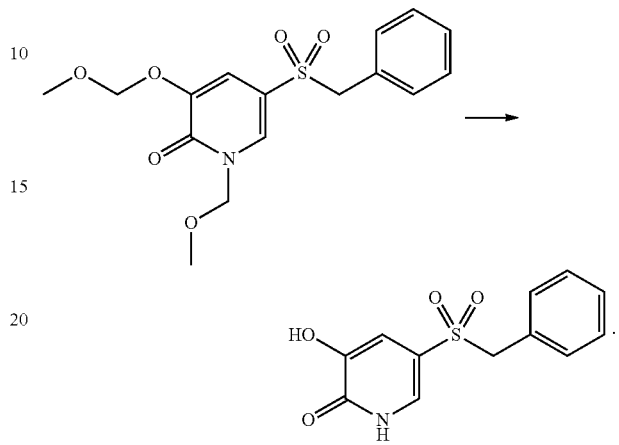

2.33. Example 33: 5-(Benzylsulfonyl)-3-hydroxypyridin-2(1H)-one

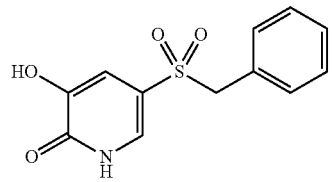 [SMILES: O=c1[nH]cc(S(=O)(=O)Cc2ccccc2)cc1O]

To a solution of 5-(benzylsulfonyl)-3-(methoxymethoxy)-1-(methoxymethyl)pyridin-2(1H)-one (Intermediate 40; 75 mg, 0.212 mmol) in dioxane (0.7 ml) and methanol (0.8 ml) was added hydrogen chloride (4.0 M in dioxane, 1.597 ml, 6.39 mmol) and the reaction irradiated in the microwave with heating to 120° C. for 10 minutes. The resulting white precipitate that had formed was filtered and washed with ethanol to yield 5-(benzylsulfonyl)-3-hydroxypyridin-2(1H)-one (25 mg, 44%).

¹H NMR (400 MHz, DMSO-d₆): δ 10.85 (br, s, 1H), 7.30-7.39 (m, 3H), 7.18-7.26 (m, 2H), 7.08-7.12 (m, 1H), 6.75-6.79 (m, 1 II) and 4.61 (s, 2H).
MS ES⁺266.

Scheme D

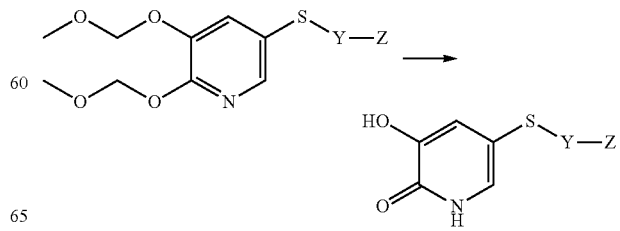

2.34. Example 34: 5-[(3-Fluorobenzyl)sulfanyl]-3-hydroxypyridin-2(1H)-one

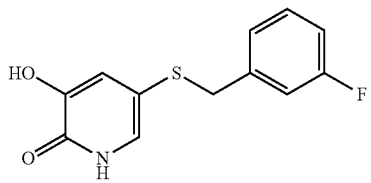 [SMILES: O=c1[nH]cc(SCc2cccc(F)c2)cc1O]

To a solution of 5-[(3-fluorobenzyl)sulfanyl]-2,3-bis(methoxymethoxy)pyridine (Intermediate 43; 690 mg, 2.03 mmol) in dioxane (4 ml) was added a solution of hydrogen chloride in dioxane (4.0 M; 2.54 ml, 10.17 mmol) and the reaction stirred for 16 hours before being concentrated in vacuo. The crude product was recrystallised from ethanol and water to yield 5-[(3-fluorobenzyl)sulfanyl]-3-hydroxypyridin-2(1H)-one as a pale grey solid (309 mg, 61%).

$^1$H NMR (400 MHz, DMSO-$d_6$): δ 11.69 (br, s, 1H), 9.23 (s, 1H), 7.26-7.37 (m, 1H), 6.95-7.10 (m, 3H), 6.65-6.75 (m, 2H), 3.96 (s, 2H).
MS ES$^+$252.

Scheme E

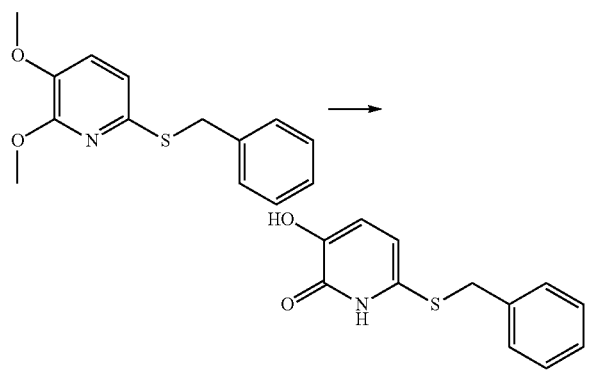

2.35. Example 35: 6-(benzylsulfanyl)-3-hydroxypyridin-2(1H)-one

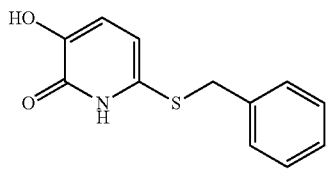 [SMILES: O=c1[nH]c(SCc2ccccc2)ccc1O]

To a solution of 6-(benzylsulfanyl)-2,3-dimethoxypyridine (Intermediate 44, 0.2 g, 0.76 mmol) in dichloromethane (1 ml) was added a solution of boron tribromide in dichloromethane (1 M, 0.77 g, 3.1 mmol) at −5° C. and reaction was stirred for 1 hour at 0° C. The temperature was gradually allowed to rise to room temperature before the mixture was stirred for a further 1 hour at room temperature. Upon cooling to 0° C. water (10 ml) was added drop-wise and the resulting mixture was filtered and the solid was washed with water (2 ml) followed by ethyl acetate (5 ml) and dried under vacuum at 40° C. to yield 6-(benzylsulfanyl)-3-hydroxypyridin-2(1H)-one (35 mg, 20%).

$^1$H NMR (400 MHz, DMSO-$d_6$): δ 7.20-7.35 (m, 5H), 6.55-6.60 (m, 1H), 6.42-6.45 (m, 1 H) and 4.15 (s, 2H).
MS ES$^+$234.

3. BIOLOGICAL EFFICACY OF COMPOUNDS OF THE INVENTION

In Vitro DAAO Enzyme Assay

The functional activity of compounds inhibiting the DAAO enzyme was determined by utilizing the co-product of the catalysis of D-Serine, $H_2O_2$ which can be quantitatively measured using the Amplex Red (Invitrogen) detection. Amplex® Red reagent is a colorless substrate that reacts with hydrogen peroxide ($H_2O_2$) with a 1:1 stoichiometry in the presence of hydrogen peroxide to produce highly fluorescent resorufin (excitation/emission maxima=570/585 nm). The changes in fluorescence were monitored by a fluorescence plate reader, Envision (Perkin Elmer) and increases in DAAO activity were readily detected upon addition of D-Serine and suppression of this response observed with the application of test compounds.

Human DAAO enzyme was supplied by the Takeda Pharmaceutical Company (Osaka) and each batch was tested and used at concentrations giving comparable levels of activity. The $K_m$ of D-Serine was measured for each enzyme batch to maintain consistency; this $K_m$ was used in subsequent assays.

On the day of the assay compounds were serially diluted in DMSO before being diluted 1:20 with assay buffer (20 mM Tris ph 7.4). A 5 µl portion of assay buffer was added to the wells of a 384 clear base black walled plate (Corning), 5 µl of diluted compound was then added via automated plate to plate transfer using the Bravo liquid handler (Agilent technologies) followed by 5 µl of human DAAO enzyme and then 5 µl D-Serine 50 mM was added to all but the negative control wells (final concentration of 10 mM). Finally 5 µl Amplex red reagent (Invitrogen) was added to all wells as per manufacturer's protocol. The plate was incubated for 60 minutes in the dark at 25° C. and the fluorescence in each well was measured in the Envision plate reader.

The IC$_{50}$ values for compounds were determined from ten point half log scale dose-response studies and represent the concentration of compound required to prevent 50% inhibition of DAAO activity in the presence of 10 mM D-Serine. Concentration response curves were generated using the average of duplicate wells for each data point and analyzed using nonlinear regression and four parameter curve fit.

Results

| Example No. | Mean IC$_{50}$ (nM) | Example No. | Mean IC$_{50}$ (nM) |
|---|---|---|---|
| 1 | 190 | 2 | 35 |
| 3 | 29 | 4 | 240 |
| 5 | 55 | 6 | 1300 |
| 7 | 210 | 8 | 190 |
| 9 | 390 | 10 | 230 |
| 11 | 47 | 12 | 79 |
| 13 | 160 | 14 | 1900 |
| 15 | 1900 | 16 | 1400 |
| 17 | 460 | 18 | 100 |
| 19 | 360 | 20 | 45 |
| 21 | 130 | 22 | 250 |
| 23 | 490 | 24 | 1000 |
| 25 | 83 | 26 | 350 |
| 27 | 140 | 28 | 260 |

-continued

| Example No. | Mean IC$_{50}$ (nM) | Example No. | Mean IC$_{50}$ (nM) |
|---|---|---|---|
| 29 | 52 | 30 | 61 |
| 31 | 130 | 32 | 170 |
| 33 | 490 | 34 | 130 |
| 35 | 1400 | | |

These results indicate that compounds of the invention have potent inhibitory activity against the DAAO enzyme. The compounds tested above exhibit IC$_{50}$ values significantly less than 5 μM, with the most potent compounds showing activity at the DAAO enzyme with IC$_{50}$ values <250 nM. Accordingly, the compounds of the invention are expected to have usefulness in the prevention or treatment of conditions, such as those discussed above, in which DAAO enzyme activity is implicated.

In addition, the compounds of the present invention possess variously advantageous pharmacological and/or toxicological profiles, when tested in a variety of standard tests for such parameters. For example, the compounds of the invention exhibit one or more potentially useful properties for in vivo use, when characterised by pharmacological and/or toxicological tests including: hERG interaction (which is an indication of potential cardiotoxicity, and measures the effects of the compounds on the human ether-a-go-go-related gene, using for example the PatchXpress 7000A platform); CypP$_{450}$ interactions (which may be measured in accordance with the FDA draft guidelines for drug interaction studies (study design, data analysis and implications for dosing and labeling) (September 2006), see www.fda.gov); phototoxicity (for example using a protocol in accordance with assay details outlined in the OECD guidelines for testing of chemicals: 432 In Vitro 3T3 Neutral Red Uptake phototoxicity test, April 2004); determination of pharmacokinetic parameters (for example following in vivo dosing via multiple routes, with plasma concentrations of compounds being determined from venous blood samples using an LC-MS/MS protocol); and in vivo receptor occupancy (determined, for example, using protocols based on Medhurst et al., *Journal of Pharmacology and Experimental Therapeutics*, 2007, 321, 1032). These standard tests for the characterisation of drug molecules are well known to the skilled person.

The invention claimed is:

1. A compound of formula (I), or a pharmaceutically acceptable salt thereof:

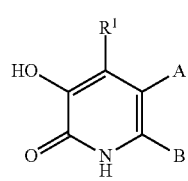

(I)

wherein
R$^1$ is chosen from a hydrogen or fluorine atom;
A represents a group —X—Y—R$^3$;
B represents R$^2$;
R$^2$ is chosen from a hydrogen atom, halogen atom, a C$_1$-C$_6$ alkyl group, a C$_3$-C$_6$ cycloalkyl group, or a C$_1$-C$_6$ alkoxy group,
wherein the C$_1$-C$_6$ alkyl group, the C$_3$-C$_6$ cycloalkyl group, and the C$_1$-C$_6$ alkoxy group are unsubstituted or substituted by at least one substituent chosen from hydroxyl, halogen, cyano, nitro, C$_1$-C$_6$ alkyl, C$_3$-C$_6$ cycloalkyl, C$_2$-C$_6$ alkenyl, C$_2$-C$_6$ alkynyl, C$_1$-C$_6$ haloalkyl, C$_1$-C$_6$ hydroxyalkyl, C$_1$-C$_6$ alkoxy, C$_1$-C$_6$ haloalkoxy, C$_1$-C$_6$ alkylcarbonyl, C$_1$-C$_6$ alkylcarbonyloxy, C$_1$-C$_6$ alkoxycarbonyl, —S(O)$_m$R$^4$ or —NR$^5$R$^6$;

m is 0, 1 or 2;
R$^4$ represents a C$_1$-C$_6$ alkyl group;
R$^5$ and R$^6$ independently are each chosen from a hydrogen atom or a C$_1$-C$_6$ alkyl group;
X and Y independently are each chosen from a bond, an oxygen atom, or a group —C(O), —S(O)$_n$, —C(O)NR$^7$, —S(O)$_2$NR$^7$, —NR$^7$,

or —CR$^7$R$^8$—, with the proviso that X and Y cannot both simultaneously represent a bond and, if X and Y are both not a bond, then at least one of X and Y represents —CR$^7$R$^8$—,
n is 0, 1 or 2;
each R$^7$ independently is chosen from a hydrogen atom or a C$_1$-C$_6$ alkyl group;
each R$^8$ independently is chosen from a hydrogen atom, a C$_1$-C$_6$ alkyl group or =CH—;
R$^3$ is chosen from a 3- to 10-membered saturated or unsaturated carbocyclic or heterocyclic ring system, wherein the ring system is unsubstituted or substituted by at least one substituent chosen from halogen, hydroxyl, cyano, oxo, C$_1$-C$_6$ alkyl, C$_2$-C$_6$ alkenyl, C$_1$-C$_6$ haloalkyl, C$_1$-C$_6$ hydroxyalkyl, C$_1$-C$_6$ alkoxy, C$_1$-C$_6$ haloalkoxy, C$_1$-C$_6$ alkylthio, C$_1$-C$_6$ alkylsulphinyl, C$_1$-C$_6$ alkylsulphonyl, C$_1$-C$_6$ alkylcarbonyl, C$_1$-C$_6$ alkylcarbonyloxy, C$_1$-C$_6$ alkoxycarbonyl, amino (—NH$_2$), —CON(R$^9$)$_2$, C$_1$-C$_6$ alkylamino, di-(C$_1$-C$_6$ alkyl)amino, C$_3$-C$_6$ cycloalkyl, C$_3$-C$_6$ cycloalkyloxy, C$_3$-C$_6$ cycloalkylmethyl, —[O]$_p$—(CH$_2$)$_q$—O—R$^{10}$, or a 4- to 6-membered saturated or unsaturated heterocyclic ring that is unsubstituted or substituted with at least one substituent chosen from C$_1$-C$_4$ alkyl or C$_1$-C$_4$ alkoxy;
each R$^9$ independently is chosen from a hydrogen atom or a C$_1$-C$_6$ alkyl group;
p is 0 or 1;
q is 1, 2, 3 or 4; and
R$^{10}$ represents a C1-C6 alkyl group.

2. The compound according to claim 1, wherein R$^3$ is not thiazolyl.

3. The compound according to claim 1, wherein R$^1$ represents a hydrogen atom.

4. The compound according to claim 1, wherein R$^2$ is chosen from a hydrogen atom, a C$_1$-C$_4$ alkyl group, or C$_3$-C$_5$ cycloalkyl group.

5. The compound according to claim 1, wherein Y is chosen from a bond or —CR$^7$R$^8$—.

6. The compound according to claim 1, wherein X is chosen from a group —S(O)$_n$ or —CHR$^7$; and Y represents a group —CHR$^7$.

7. The compound according to claim 1, wherein X represents —CR$^7$R$^8$—.

8. The compound according to claim 1, wherein R$^3$ is chosen from phenyl, pyridinyl, oxazolyl, pyrazinyl, cyclopropyl, cyclopentyl, cyclohexyl, tetrahydropyranyl, 2,3-dihydrobenzofuranyl, pyrimidinyl, imidazo[1,2-a]pyridinyl, pyrazolyl or piperidinyl.

9. The compound according to claim 1, wherein $R^3$ is chosen from a 5 or 6-membered unsaturated carbocyclic or heterocyclic ring system, wherein the heterocyclic ring system comprises one or two ring heteroatoms independently chosen from nitrogen and oxygen, and wherein the carbocyclic or heterocyclic ring system is unsubstituted or substituted by one, two, three or four substituents independently chosen from fluorine, chlorine, bromine, hydroxyl, cyano, oxo, $C_1$-$C_4$ alkyl, $C_2$-$C_4$ alkenyl, $C_1$-$C_2$ haloalkyl, $C_1$-$C_2$ hydroxyalkyl, $C_1$-$C_4$ alkoxy, $C_1$-$C_2$ haloalkoxy, $C_1$-$C_4$ alkylthio, $C_1$-$C_4$ alkylsulphinyl, $C_1$-$C_4$ alkylsulphonyl, $C_1$-$C_4$ alkylcarbonyl, $C_1$-$C_4$ alkylcarbonyloxy, $C_1$-$C_4$ alkoxycarbonyl, amino, carboxamido, $C_1$-$C_4$ alkylamino, di-($C_1$-$C_4$ alkyl) amino, $C_3$-$C_4$ cycloalkyl, $C_3$-$C_4$ cycloalkyloxy, $C_3$-$C_4$ cycloalkylmethyl, —[O]$_p$—(CH$_2$)$_q$—O—R$^{10}$, or a 4- to 5-membered saturated or unsaturated heterocyclic ring unsubstituted or substituted by methyl or methoxy.

10. The compound according to claim 1, chosen from:
5-(Benzylsulfanyl)-3-hydroxypyridin-2(1H)-one,
5-[(4-Chlorobenzyl)sulfanyl]-3-hydroxypyridin-2(1H)-one,
3-Hydroxy-5-[(4-methylbenzyl)sulfanyl]pyridin-2(1H)-one,
3-Hydroxy-5-[(3-methylbenzyl)sulfanyl]pyridin-2(1H)-one,
5-[(3-Chlorobenzyl)sulfanyl]-3-hydroxypyridin-2(1H)-one,
3-Hydroxy-5-[(1-phenylethyl)sulfanyl]pyridin-2(1H)-one,
5-[(2-Chlorobenzyl)sulfanyl]-3-hydroxypyridin-2(1H)-one,
3-Hydroxy-5-{[3-(trifluoromethyl)benzyl]sulfanyl}pyridin-2(1H)-one,
3-Hydroxy-5-[(2-methylbenzyl)sulfanyl]pyridin-2(1H)-one,
5-[(3-Chloro-5-fluorobenzyl)sulfanyl]-3-hydroxypyridin-2(1H)-one,
5-[(4-Fluorobenzyl)sulfanyl]-3-hydroxypyridin-2(1H)-one,
5-[(4-Ethylbenzyl)sulfanyl]-3-hydroxypyridin-2(1H)-one,
3-Hydroxy-5-({[6-(trifluoromethyl)pyridin-3-yl]methyl}-sulfanyl)pyridin-2(1H)-one,
3-Hydroxy-5-{[(3-methylpyridin-2-yl)methyl]sulfanyl}pyridin-2(1H)-one,
5-{[(3,5-Dimethyl-1,2-oxazol-4-yl)methyl]sulfanyl}-3-hydroxypyridin-2(1H)-one,
3-Hydroxy-5-{[(2-methyl-1,3-oxazol-4-yl)methyl]sulfanyl}-pyridin-2(1H)-one,
3-Hydroxy-5-[(pyridin-2-ylmethyl)sulfanyl]pyridin-2(1H)-one,
3-Hydroxy-5-[(pyridin-4-ylmethyl)sulfanyl]pyridin-2(1H)-one,
5-{[(5-Chloropyridin-2-yl)methyl]sulfanyl}-3-hydroxypyridin-2(1H)-one,
5-[(3,4-Difluorobenzyl)sulfanyl]-3-hydroxypyridin-2(1H)-one,
3-Hydroxy-5-[(4-methoxybenzyl)sulfanyl]pyridin-2(1H)-one,
3-Hydroxy-5-[(pyridin-3-ylmethyl)sulfanyl]pyridin-2(1H)-one,
3-Hydroxy-5-{[(5-methylpyridin-2-yl)methyl]sulfanyl}pyridin-2(1H)-one,
3-Hydroxy-5-[(pyrazin-2-ylmethyl)sulfanyl]pyridin-2(1H)-one,
3-Hydroxy-5-{[(6-methoxypyridin-3-yl)methyl]-sulfanyl}-pyridin-2(1H)-one,
3-Hydroxy-5-(2-methylphenethyl)pyridin-2(1H)-one,
3-Hydroxy-5-(2-phenylethyl)pyridin-2(1H)-one,
3-Hydroxy-5-[2-(3-methylphenyl)ethyl]pyridin-2(1H)-one,
3-Hydroxy-5-[2-(4-methylphenyl)ethyl]pyridin-2(1H)-one,
5-[2-(4-Fluorophenyl)ethyl]-3-hydroxypyridin-2(1H)-one,
5-[2-(3-Fluorophenyl)ethyl]-3-hydroxypyridin-2(1H)-one,
5-[2-(2-Fluorophenyl)ethyl]-3-hydroxypyridin-2(1H)-one,
5-(Benzylsulfonyl)-3-hydroxypyridin-2(1H)-one,
5-[(3-Fluorobenzyl)sulfanyl]-3-hydroxypyridin-2(1H)-one,
or a pharmaceutically acceptable salt thereof.

11. A process for the preparation of the compound according to claim 1, comprising:
when X represents a sulphur atom or when X is a bond and Y represents a sulphur atom, reacting a compound of formula (IIa)

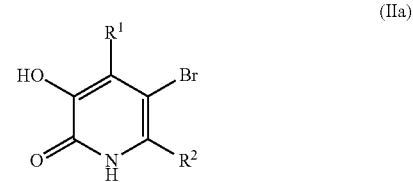

with a compound of formula (III), HS—[Y]$_t$—R$^3$, wherein t is chosen from 0 or 1;
and optionally thereafter carrying out at least one of the following procedures:
converting the compound according to claim 1 into another compound according to claim 1;
removing any protecting groups; or
forming a pharmaceutically acceptable salt.

12. A pharmaceutical composition comprising the compound according to claim 1, and a pharmaceutically acceptable adjuvant, diluent or carrier.

13. A method of treating a condition whose development or symptoms are linked to DAAO enzyme activity comprising administering to a patient in need thereof a pharmaceutically effective amount of a compound according to claim 1.

14. A method of treating schizophrenia, schizophreniform disorder, schizoaffective disorder, cognitive disorders or pain comprising administering to a patient in need thereof a pharmaceutically effective amount of a compound according to claim 1.

15. A combination comprising the compound according to claim 1, and at least one additional agent chosen from carbamazepine, olanzapine, quetiapine, verapamil, lamotrigine, oxcarbazepine, risperidone, aripiprazole, ziprasidone or lithium.

16. A process for the preparation of the compound according to claim 1, comprising:
when X represents SO or when X is a bond and Y represents SO, oxidising a compound of formula (IVa) with a suitable oxidising agent, wherein $P^1$ represents a protecting group,

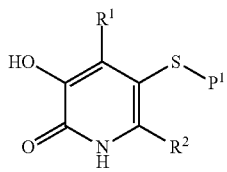
(IVa)

followed by reaction with a compound of formula (V), $L^1$-$[Y]_w$—$R^3$, wherein w is chosen from 0 or 1 and $L^1$ represents a leaving group; and
optionally thereafter carrying out at least one of the following procedures:
converting the compound according to claim 1 into another compound according to claim 1;
removing any protecting groups; or
forming a pharmaceutically acceptable salt.

17. A process for the preparation of the compound according to claim 1, comprising:
when X represents $SO_2$ or when X is a bond and Y represents $SO_2$, oxidising a compound of formula (IVa) with a suitable oxidising agent, wherein $P^1$ represents a protecting group,

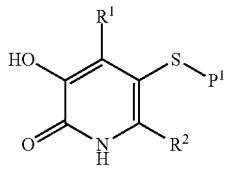
(IVa)

followed by reaction with a compound of formula (V), $L^1$-$[Y]_w$—$R^3$, wherein w is chosen from 0 or 1 and $L^1$ represents a leaving group; and
optionally thereafter carrying out at least one of the following procedures:
converting the compound according to claim into another compound according to claim;
removing any protecting groups; or
forming a pharmaceutically acceptable salt.

18. A process for the preparation of the compound according to claim 1, comprising:
when X represents an oxygen atom or when X is a bond and Y represents an oxygen atom, reacting a compound of formula (IIa)

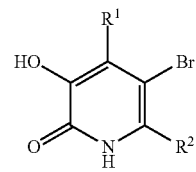
(IIa)

with a compound of formula (VI), HO—$[Y]_z$—$R^3$, wherein z is chosen from 0 or 1; and
optionally thereafter carrying out at least one of the following procedures:
converting the compound according to claim 1 into another compound according to claim 1;
removing any protecting groups; or
forming a pharmaceutically acceptable salt.

19. A process for the preparation of the compound according to claim 1, comprising:
when X represents C(O) or when X is a bond and Y represents C(O), reacting a compound of formula (IIa) with carbon dioxide,

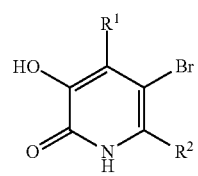
(IIa)

followed by (a) addition of an activating agent and (b) reaction with a compound of formula (Va), M-$[Y]_w$—$R^3$, wherein
M is chosen from Li or $MgR^{20}$,
$R^{20}$ represents a halogen atom,
w is chosen from 0 or 1; and
optionally thereafter carrying out at least one of the following procedures:
converting the compound according to claim 1 into another compound according to claim 1;
removing any protecting groups; or
forming a pharmaceutically acceptable salt.

20. A process for the preparation of the compound according to claim 1, comprising;
when X represents —C(O)$NR^7$ or when X is a bond and Y represents —C(O)$NR^7$, reacting a compound of formula (VIIa)

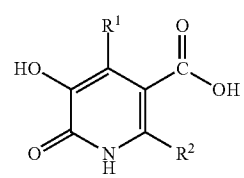
(VIIa)

with a compound of formula (VIII), $R^7HN$—$[Y]_g$—$R^3$, wherein g is chosen from 0 or 1; and
optionally thereafter carrying out at least one of the following procedures:
converting the compound according to claim 1 into another compound according to claim 1;
removing any protecting groups; or
forming a pharmaceutically acceptable salt.

21. A process for the preparation of the compound according to claim 1, comprising;
when X represents —S(O)$_2$NR$^7$ or when X is a bond and Y represents —S(O)$_2$NR$^7$, reacting a compound of formula (IIa)

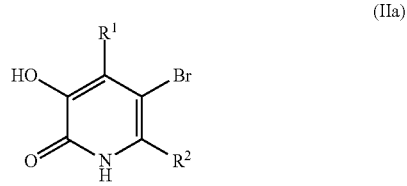
(IIa)

with sulphur dioxide, followed by addition of an oxidising-chlorinating agent and then reaction with a compound of formula (VIII), R$^7$HN—[Y]$_g$—R$^3$, wherein g is chosen from 0 or 1; and
optionally thereafter carrying out at least one of the following procedures:
converting the compound according to claim 1 into another compound according to claim 1;
removing any protecting groups; or
forming a pharmaceutically acceptable salt.

22. A process for the preparation of the compound according to claim 1, comprising:
when X represents —NR$^7$ or when X is a bond and Y represents —NR$^7$, reacting a compound of formula (IIa)

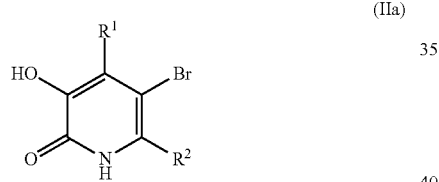
(IIa)

with a compound of formula (VIII), R$^7$HN—[Y]$_g$—R$^3$, wherein g is chosen from 0 or 1; and
optionally thereafter carrying out at least one of the following procedures:
converting the compound according to claim 1 into another compound according to claim 1;
removing any protecting groups; or
forming a pharmaceutically acceptable salt.

23. A process for the preparation of the compound according to claim 1, comprising:
when X represents —CR$^7$R$^8$— or when X is a bond and Y represents —CR$^7$R$^8$— and R$^7$ and R$^8$ each independently represent a C$_1$-C$_6$ alkyl group, reacting a compound of formula (IIa)

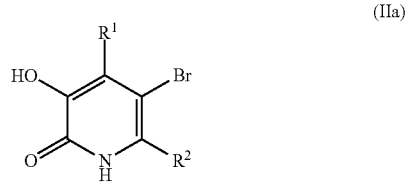
(IIa)

with a compound of formula (IX), L$^2$-CR$^{7'}$R$^{8'}$—[Y]$_h$—R$^3$, wherein
h is chosen from 0 or 1,
L$^2$ represents a leaving group, and
R$^{7'}$ and R$^{8'}$ each independently represent a C$_1$-C$_6$ alkyl group; and
optionally thereafter carrying out at least one of the following procedures:
converting the compound according to claim 1 into another compound according to claim 1;
removing any protecting groups; or
forming a pharmaceutically acceptable salt.

24. A process for the preparation of the compound according to claim 1, comprising:
when X represents —CR$^7$R$^8$— or when X is a bond and Y represents —CR$^7$R$^8$— and R$^7$ and R$^8$ each independently are chosen from a hydrogen atom or a C$_1$-C$_6$ alkyl group, reacting a compound of formula (IIa)

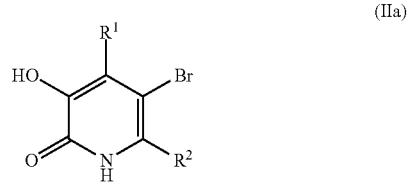
(IIa)

with a compound of formula (IXa), R$^7$C(O)—[Y]$_h$—R$^3$, followed by a hydrogenation reaction, wherein
h is chosen from 0 or 1, and
R$^7$ and R$^8$ do not simultaneously represent a C$_1$-C$_6$ alkyl group, and
optionally thereafter carrying out at least one of the following procedures:
converting the compound according to claim 1 into another compound according to claim 1;
removing any protecting groups; or
forming a pharmaceutically acceptable salt.

25. A process for the preparation of the compound according to claim 1, comprising:
when X and Y represent —CHR$^7$, hydrogenating a compound of formula (Xa)

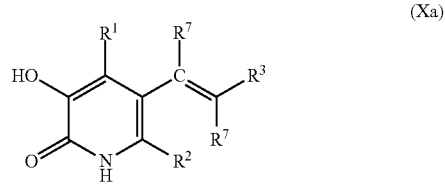
(Xa)

and optionally thereafter carrying out at least one of the following procedures:
converting the compound according to claim 1 into another compound according to claim 1;
removing any protecting groups; or
forming a pharmaceutically acceptable salt.

26. A process for the preparation of the compound according to claim 1, comprising:
when X represents —CR$^7$R$^8$— or when X is a bond and Y represents —CR$^7$R$^8$— and R$^8$ is =CH, reacting a compound of formula (XIa), wherein R$^{22}$ is chosen from a hydrogen atom or a C$_1$-C$_6$ alkyl group,

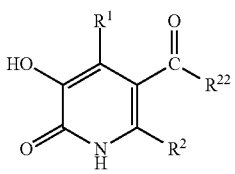 (XIa)

with a compound of formula (IXb), $R^{24}$—$CH(R^{26})$—$[Y]_h$—$R^3$, wherein
h is chosen from 0 or 1,
$R^{24}$ represents a phosphonate group, and
$R^{26}$ is chosen from a hydrogen atom or a $C_1$-$C_6$ alkyl group, and
optionally thereafter carrying out at least one of the following procedures:
  converting the compound according to claim 1 into another compound according to claim 1;
  removing any protecting groups; or
  forming a pharmaceutically acceptable salt.

27. A process for the preparation of the compound according to claim 1, comprising:
when X represents a group

or when X is a bond and Y represents a group

, reacting a compound of formula (XIIa), wherein k is chosen from 0 or 1,

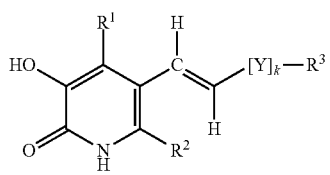 (XIIa)

with diodomethane and zinc-copper couple; and
optionally thereafter carrying out at least one of the following procedures:
  converting the compound according to claim 1 into another compound according to claim 1;
  removing any protecting groups; or
  forming a pharmaceutically acceptable salt.

28. A process for the preparation of the compound according to claim 1, comprising:
when X represents a group

or when X is a bond and Y represents a group

, reacting a compound of formula (XIIIa), wherein l is chosen from 0 or 1,

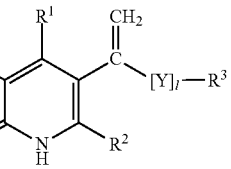 (XIIIa)

with diodomethane and zinc-copper couple; and
optionally thereafter carrying out at least one of the following procedures:
  converting the compound according to claim 1 into another compound according to claim 1;
  removing any protecting groups; or
  forming a pharmaceutically acceptable salt.

* * * * *

UNITED STATES PATENT AND TRADEMARK OFFICE
CERTIFICATE OF CORRECTION

PATENT NO. : 9,180,122 B2  
APPLICATION NO. : 14/131343  
DATED : November 10, 2015  
INVENTOR(S) : William Farnaby et al.

Page 1 of 1

It is certified that error appears in the above-identified patent and that said Letters Patent is hereby corrected as shown below:

Title page, item 57 (Abstract), Line 6, "are—processes" should read as: --are: processes--.

Signed and Sealed this
Fifteenth Day of March, 2016

Michelle K. Lee
*Director of the United States Patent and Trademark Office*